(12) United States Patent
Yamazaki et al.

(10) Patent No.: US 11,013,474 B2
(45) Date of Patent: May 25, 2021

(54) X-RAY COMPUTED TOMOGRAPHY APPARATUS

(71) Applicant: Canon Medical Systems Corporation, Otawara (JP)

(72) Inventors: Takayuki Yamazaki, Nasushiobara (JP); Makoto Hayashibara, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 5 days.

(21) Appl. No.: 16/055,848

(22) Filed: Aug. 6, 2018

(65) Prior Publication Data

US 2019/0046128 A1 Feb. 14, 2019

(30) Foreign Application Priority Data

Aug. 8, 2017 (JP) .............................. JP2017-153427
Jul. 31, 2018 (JP) .............................. JP2018-143736

(51) Int. Cl.
*A61B 6/03* (2006.01)
*A61B 6/08* (2006.01)
*A61B 6/00* (2006.01)
*A61B 5/107* (2006.01)
*A61B 5/00* (2006.01)

(52) U.S. Cl.
CPC ............ *A61B 6/032* (2013.01); *A61B 5/0082* (2013.01); *A61B 5/1077* (2013.01); *A61B 6/08* (2013.01); *A61B 6/4035* (2013.01); *A61B 6/488* (2013.01); *A61B 6/544* (2013.01); *A61B 6/545* (2013.01); *A61B 6/4447* (2013.01); *A61B 6/461* (2013.01); *A61B 6/5205* (2013.01)

(58) Field of Classification Search
None
See application file for complete search history.

(56) References Cited

U.S. PATENT DOCUMENTS 10,004,465 B2 * 6/2018 Krauss .................... A61B 6/032
10,034,648 B2 * 7/2018 Lin ......................... A61B 6/025
10,251,612 B2 * 4/2019 Lin ......................... A61B 6/032
(Continued)

FOREIGN PATENT DOCUMENTS

| JP | 2006-26417 | 2/2006 |
| JP | 2006-116137 | 5/2006 |
| JP | 2014-528284 | 10/2014 |

OTHER PUBLICATIONS

Boone, J., et al. "Size-Specific Dose Estimates (SSDE) in Pediatric and Adult Body CT Examinations", AAPM (American Association of Physicists in Medicine) Report, No. 204, 2011, 30 pages.
(Continued)

*Primary Examiner* — Thomas R Artman
(74) *Attorney, Agent, or Firm* — Oblon, McClelland, Maier & Neustadt, L.L.P.

(57) ABSTRACT

According to one embodiment, an X-ray computed tomography apparatus includes a gantry that performs X-ray CT imaging; a bed that movably supports a table top on which a subject lies; an optical emitter that is provided on the gantry and emits a light beam to the subject lying on the table top; and an estimator that estimates a shape index value of a cross section of the subject in an imaging range by utilizing the light beam emitted to the subject.

13 Claims, 16 Drawing Sheets

(56) References Cited

U.S. PATENT DOCUMENTS

| | | |
|---|---|---|
| 2006/0018435 A1 | 1/2006 | Toth et al. |
| 2014/0270053 A1* | 9/2014 | Larson |
| 2016/0262714 A1* | 9/2016 | Krauss ................. A61B 5/0064 |
| 2017/0196529 A1* | 7/2017 | Lin ........................ A61B 6/541 |
| 2017/0224298 A1* | 8/2017 | Hannemann ........... A61B 5/744 |
| 2018/0040121 A1* | 2/2018 | Lin ....................... A61B 5/0035 |
| 2019/0046128 A1* | 2/2019 | Yamazaki ................ A61B 6/08 |

OTHER PUBLICATIONS

McCollough, C., et al. "Use of Water Equivalent Diameter for Calculating Patient Size and Size-Specific Dose Estimates (SSDE) in CT", AAPM (American Association of Physicists in Medicine) Report, No. 220, 2014, 23 pages.

\* cited by examiner

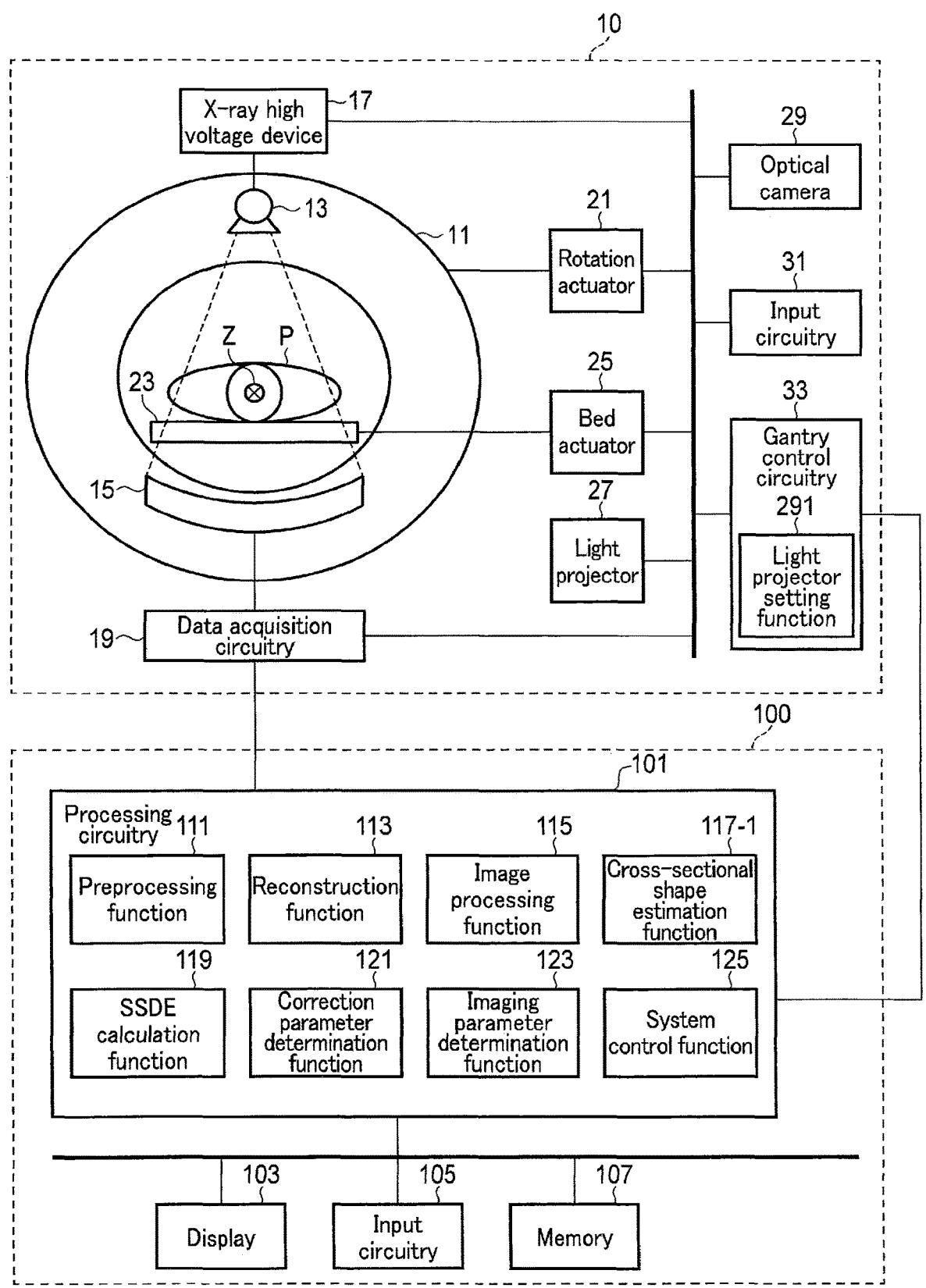
F I G. 1

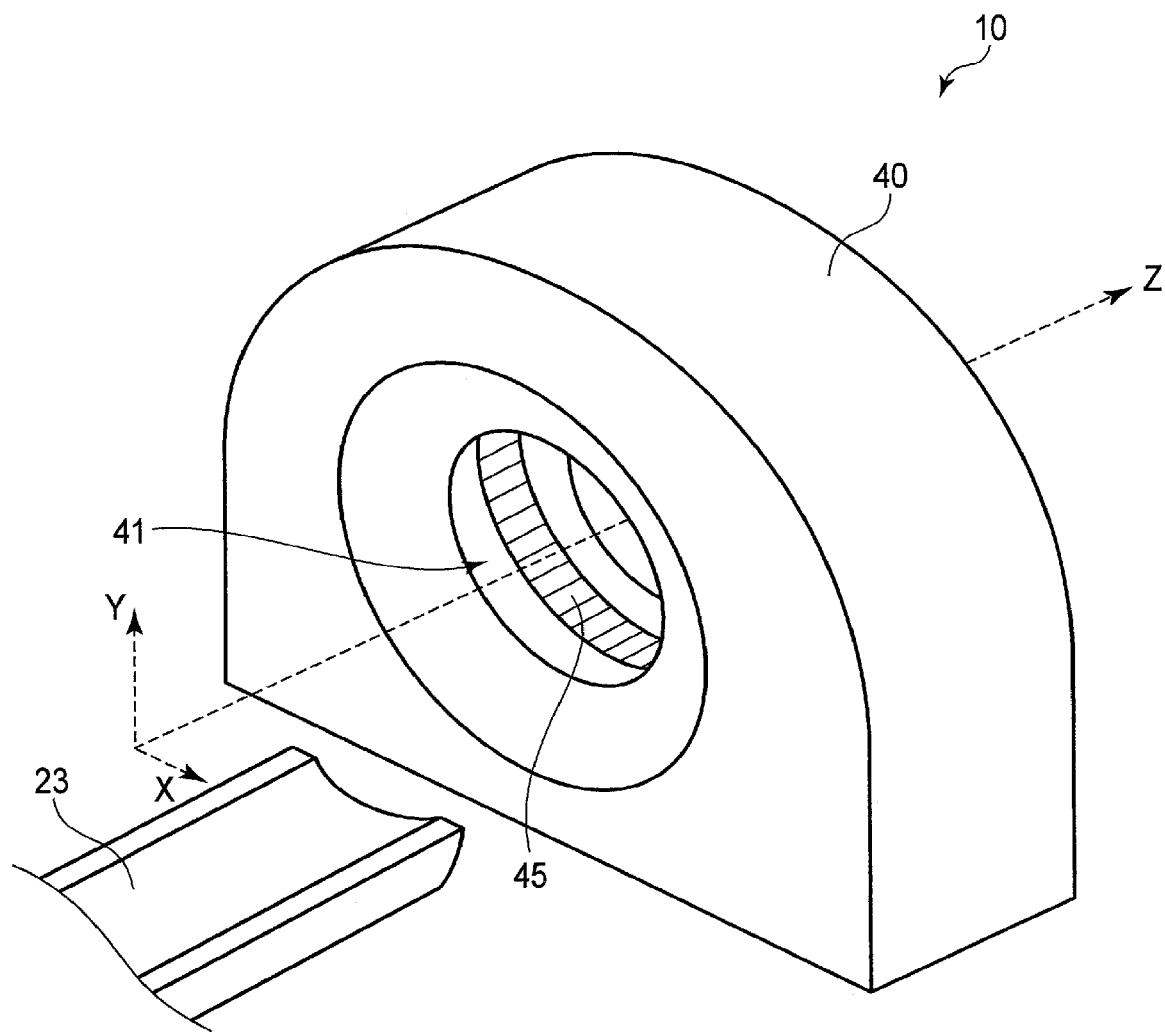
F I G. 2

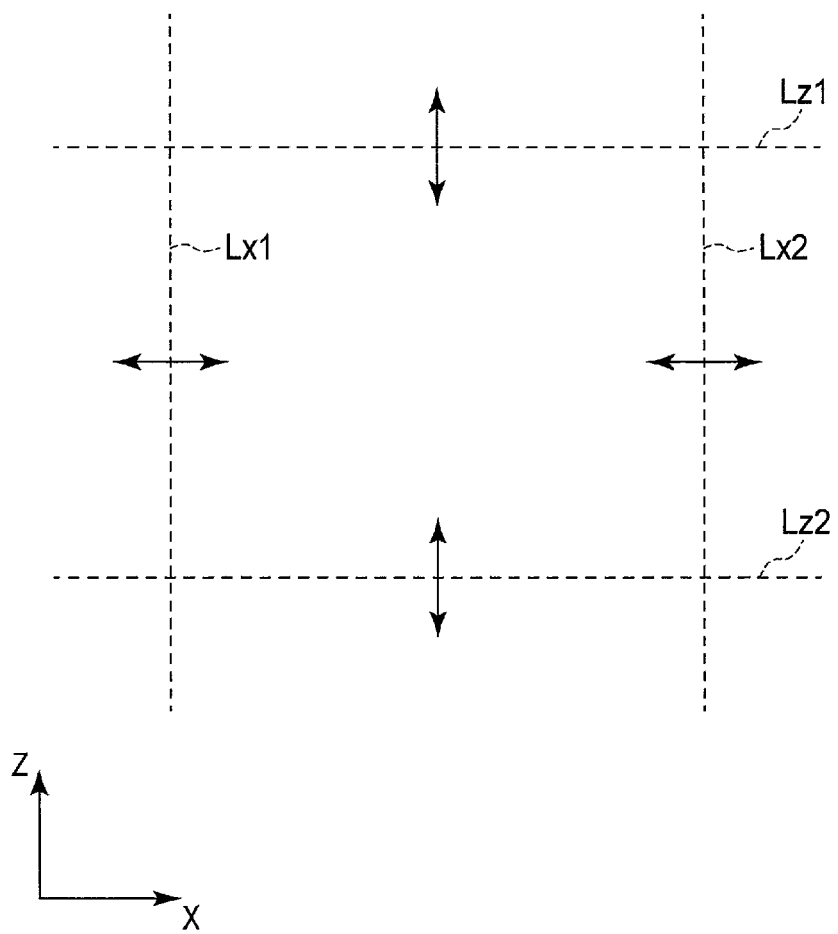
F I G. 4

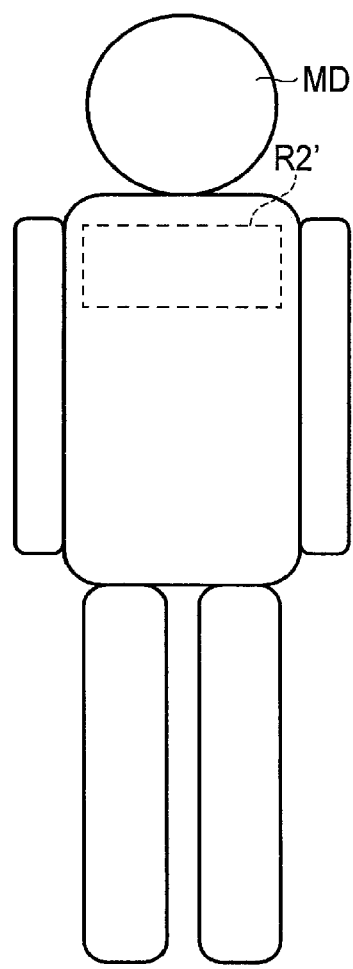
F I G. 8
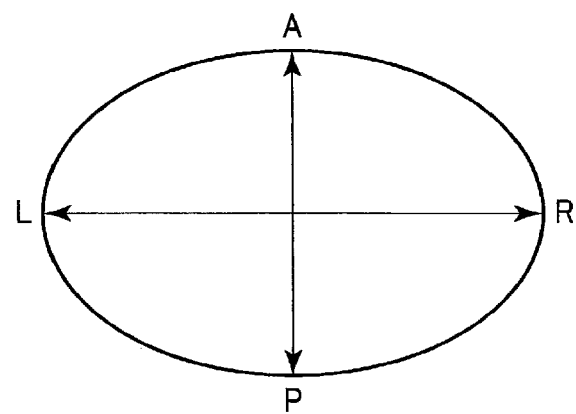
F I G. 9

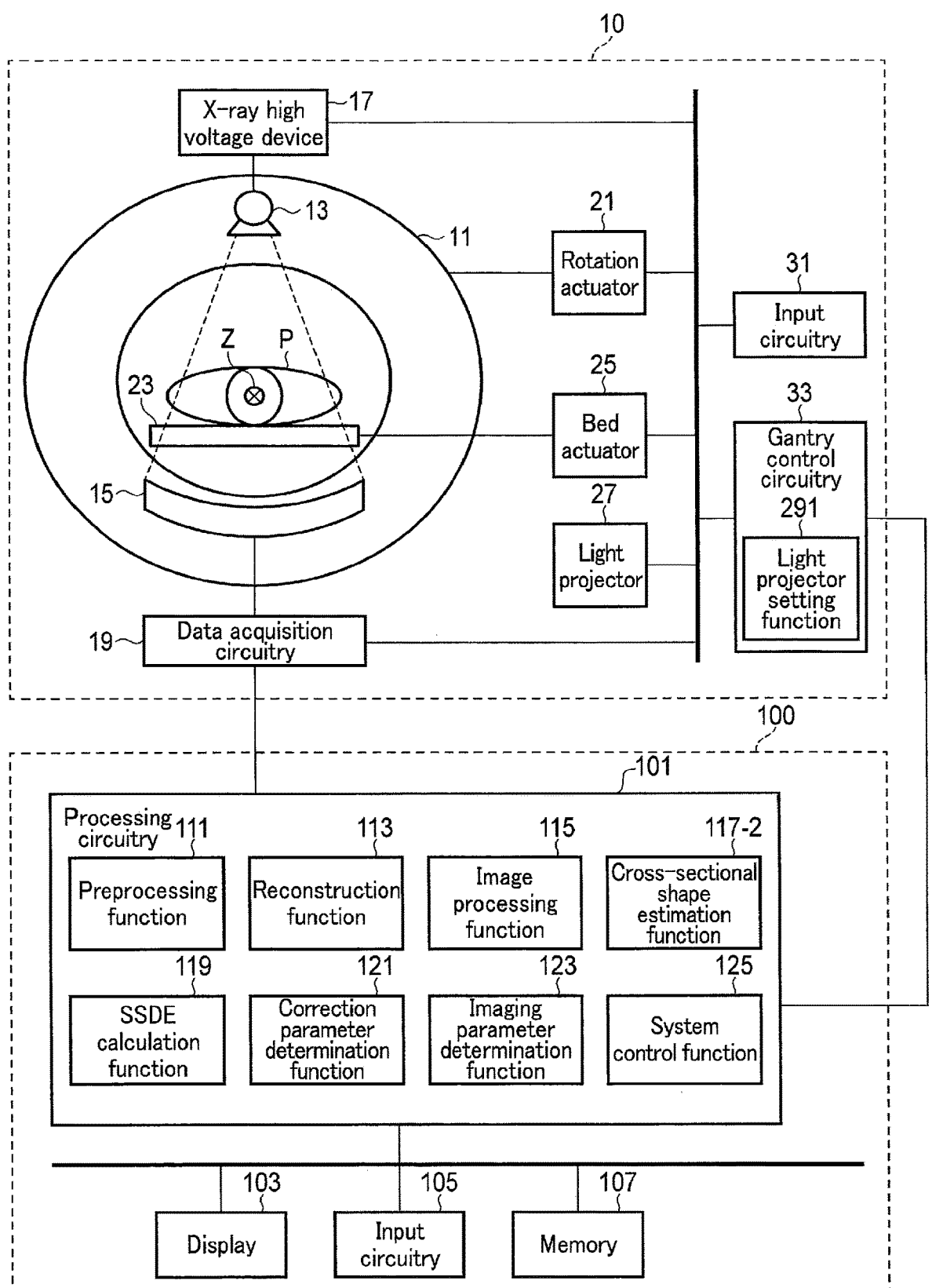
F I G. 11

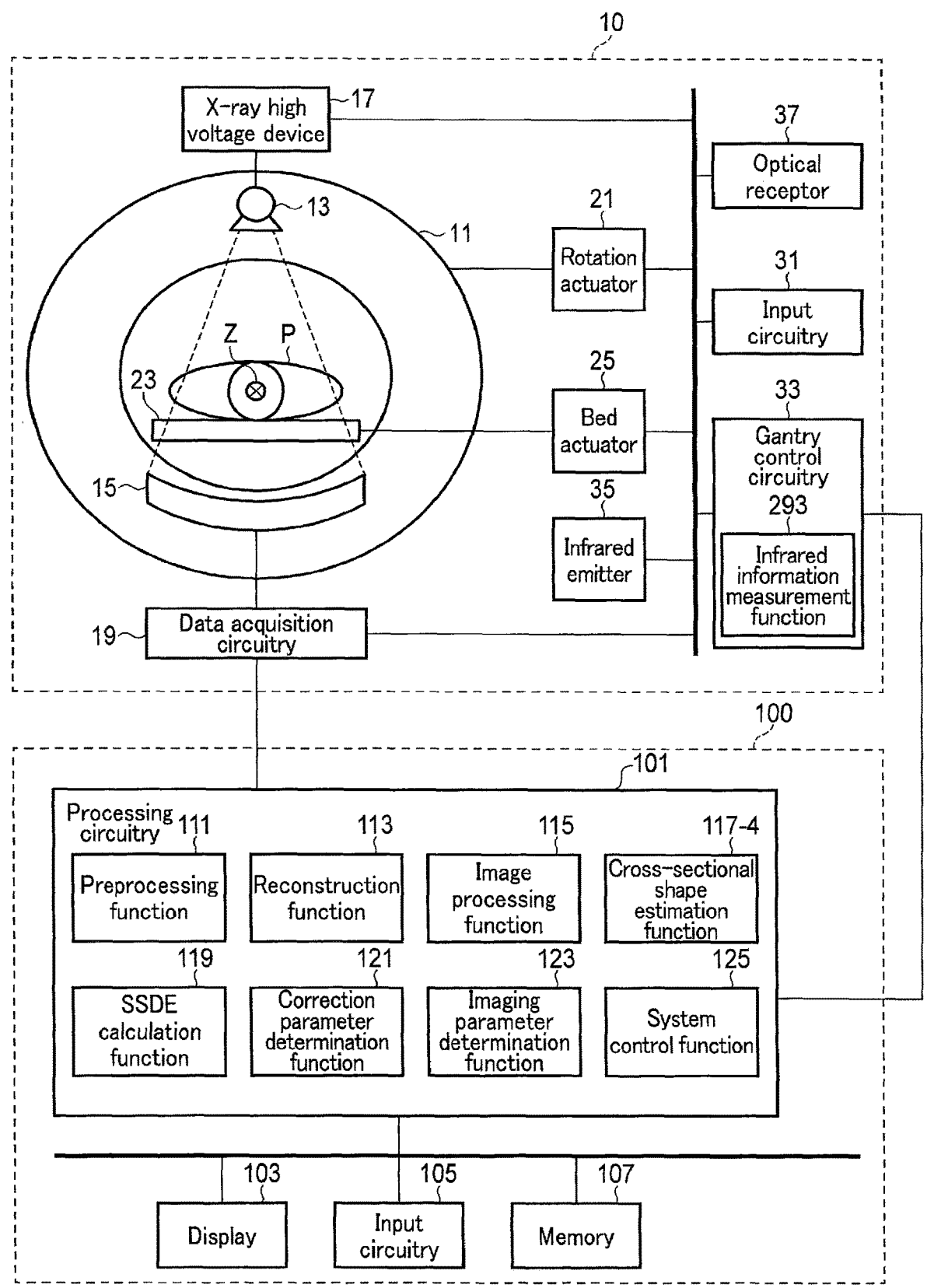
F I G. 16

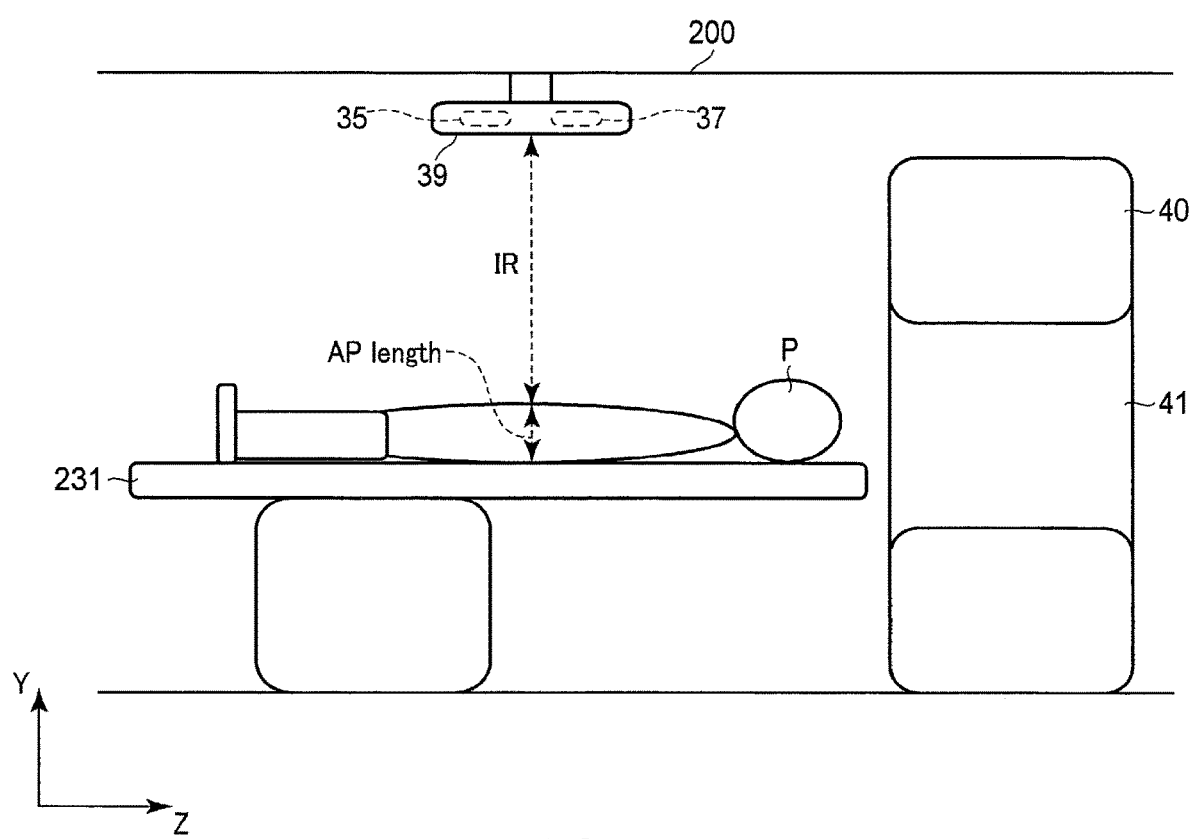
F I G. 18

X-RAY COMPUTED TOMOGRAPHY APPARATUS

CROSS-REFERENCE TO RELATED APPLICATIONS

This application is based upon and claims the benefit of priority from the Japanese Patent Application No. 2017-153427, filed Aug. 8, 2017, and the Japanese Patent Application No. 2018-143736, filed Jul. 31, 2018 the entire contents of all of which are incorporated herein by reference.

FIELD

Embodiments described herein relate generally to an X-ray computed tomography apparatus.

BACKGROUND

SSDE (Size-Specific Dose Estimates) is known as a dose index in CT imaging. SSDE is calculated based on a cross-sectional shape of an object that was estimated by using a positioning image. Thus, to estimate a cross-sectional shape, positioning imaging is necessary.

On the other hand, at a stage prior to CT imaging, positioning of an object is performed using a light projector that emits a light beam indicating a reference line of an imaging range. In recent years, positioning imaging for positioning can be omitted by using a light projector that emits a light beam indicating an outer frame of an imaging range. However, when positioning imaging is omitted, a cross-sectional shape cannot be estimated, and accordingly, a predicted dose index, such as SSDE, cannot be calculated.

BRIEF DESCRIPTION OF THE DRAWINGS

FIG. 1 is a diagram showing a configuration of an X-ray computed tomography apparatus according to a first embodiment.

FIG. 2 is a schematic view showing an appearance of a gantry according to the first embodiment.

FIG. 4 is a diagram showing an example of visible light beams representing frame lines constituting an outer frame of a CT imaging range.

FIG. 8 is a schematic view showing an example of data on a human body model stored in the memory shown in FIG. 1.

FIG. 9 is a schematic view of an example of an imaged cross section of the human body model shown in FIG. 8.

FIG. 11 is a diagram showing a configuration of an X-ray computed tomography apparatus according to a second embodiment.

FIG. 16 is a diagram showing a configuration of an X-ray computed tomography apparatus according to a fourth embodiment.

FIG. 18 is a schematic diagram illustrating an overview of estimation of a cross-sectional shape index value utilizing infrared according to the fourth embodiment.

DETAILED DESCRIPTION

Figure 3:
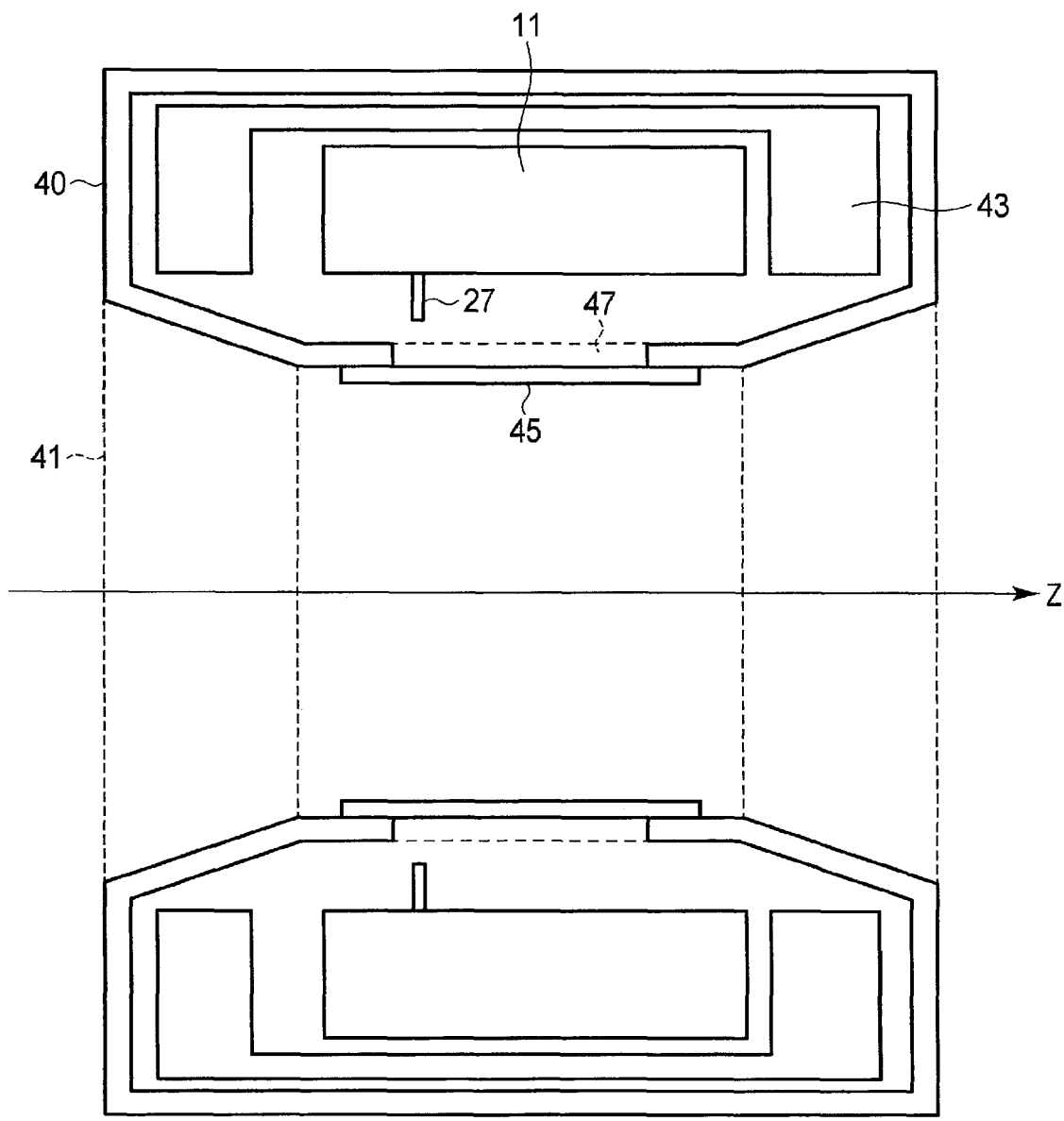
FIG. 3 is a cross-sectional view including a Z axis of the gantry shown in FIG. 2.

In general, according to one embodiment, an X-ray computed tomography apparatus includes a gantry, a bed, an optical emitter, and processing circuitry. The gantry performs X-ray CT imaging. The bed movably supports a table top on which a subject lies. The optical emitter is mounted on the gantry and emits light beams to the subject lying on the table top. The processing circuitry estimates a cross-sectional shape index value of the subject in the imaging range utilizing the light beams emitted to the subject.

An X-ray computed tomography apparatus according to the present embodiment will be described in detail with reference to the accompanying drawings.

First Embodiment

FIG. 1 is a diagram showing a configuration of an X-ray computed tomography apparatus according to a first embodiment. As shown in FIG. 1, the X-ray computed tomography apparatus of the first embodiment includes a gantry 10 and a console 100. For example, the gantry 10 is placed in an examination room, and the console 100 is placed in a control room adjacent to the examination room. The gantry 10 and the console 100 are communicably connected to each other. The gantry 10 includes an imaging mechanism configured to perform X-ray CT imaging of a subject P, such as a patient. The console 100 is a computer that controls the gantry 10.

As shown in FIG. 1, the gantry 10 includes an almost cylindrical rotation frame 11 with a bore. The rotation frame 11 is also referred to as a rotation unit. As shown in FIG. 1, an X-ray tube 13 and an X-ray detector 15, arranged to face each other via the bore, are mounted on the rotation frame 11. The rotation frame 11 is a metal frame made of, for example, aluminum, in an annular shape. As will be detailed later, the gantry 10 includes a main frame made of metal, such as aluminum. The main frame is also referred to as a stationary unit. The rotation frame 11 is rotatably supported by the main frame.

The X-ray tube 13 generates X-rays. The X-ray tube 13 is a vacuum tube which holds a cathode that generates thermoelectrons, and an anode that generates X-rays by receiving the thermoelectrons that have traveled from the cathode. The X-ray tube 13 is connected to an X-ray high voltage device 17 via a high voltage cable.

The X-ray high voltage device 17 may adopt any type of high voltage generator such as a transformer type X-ray high voltage generator, a constant voltage type X-ray high voltage generator, a capacitor type X-ray high voltage generator, or an inverter type X-ray high voltage generator. The X-ray high voltage device 17 is attached, for example, to the rotation frame 11. The X-ray high voltage device 17 adjusts a tube voltage applied to the X-ray tube 13, a tube current, and the focus size of the X-rays in accordance with control by a gantry control circuitry 33.

As shown in FIG. 1, the rotation frame 11 rotates about a center axis Z at a predetermined angular velocity upon receiving power from a rotation actuator 21. For the rotation actuator 21, any motor, for example, a direct drive motor or a servo motor, is used. The rotation actuator 21 is housed in, for example, the gantry 10. The rotation actuator 21 generates power to rotate the rotation frame 11 upon receiving a drive signal from the gantry control circuitry 33.

A CT imaging range (FOV: Field Of View) is set at the bore of the rotation frame 11. A table top supported by the bed 23 is inserted into the bore of the rotation frame 11. The patient P is placed on the table top. The bed 23 movably supports the table top. The bed 23 houses a bed actuator 25. Upon receipt of a drive signal from the gantry control circuitry 33, the bed actuator 25 generates power to move the table top back and forth, up and down, and left and right. The bed 23 moves the table top for positioning so that an imaging target area of the patient P can fit in the CT imaging range.

The X-ray detector 15 detects the X-rays generated by the X-ray tube 13. Specifically, the X-ray detector 15 includes a plurality of detection elements arranged on a two-dimensional curved surface. Each of the detection elements includes a scintillator and a photoelectric conversion element. The scintillator is formed of a material that converts X-rays into photons. The scintillator converts the applied X-rays into photons of the number corresponding to the intensity of the applied X-rays. The photoelectric conversion element is a circuit element that amplifies photons received from the scintillator and converts the received photons into an electrical signal. For example, a photomultiplier tube, a photodiode, or the like is applied as the photoelectric conversion element. The detection elements may adopt an indirect conversion-type detection element, which converts X-rays into photons and then detects the photons; or a direct conversion-type detection element, which directly converts X-rays into an electrical signal.

The X-ray detector 15 is connected to data acquisition circuitry 19. In accordance with the instruction from the gantry control circuitry 33, the data acquisition circuitry 19 reads from the X-ray detector 15 an electrical signal corresponding to the intensity of X-rays detected by the X-ray detector 15, and acquires raw data with a digital value corresponding to the dose of X-rays during a view period. The data acquisition circuitry 19 is implemented by, for example, an ASIC (Application Specific Integrated Circuit) on which a circuit element capable of generating count data is mounted.

A light projector 27 is mounted on the rotation frame 11. In accordance with the instructions from the gantry control circuitry 33, the light projector 27 projects visible light beams (projection laser) indicating reference lines of the CT imaging range to the table top inserted in the bore, or to the patient P placed on the table top. The visible light beams are projected for the positioning of the patient P.

An optical camera 29 is an optical imaging unit that generates an optical image of the patient P as a subject irradiated with the visible light beams from the light projector 27. The optical camera 29 may be located at any position where the patient P irradiated with the visible light beams from the light projector can be imaged. The optical image is transmitted to the console 100.

Input circuitry 31 receives various instructions from the user about positioning of the bed 23 or the light projector 27. Specifically, the input circuitry 31 includes an input device and an input interface. The input device includes a switch button—or the like—of hardware or software. The input interface is connected to the gantry control circuitry 33. The input interface converts an operation input from the user via the input device into an electric signal, and outputs the electric signal to the gantry control circuitry 33.

The gantry control circuitry 33 synchronously controls the X-ray high voltage device 17, the data acquisition circuitry 19, the rotation actuator 21, the bed actuator 25, etc. to perform X-ray CT imaging in accordance with imaging conditions transmitted from the processing circuitry 101 of the console 100. The gantry control circuitry 33 controls the rotation actuator 21 and the light projector 27 for positioning or the like of the patient P. The gantry control circuitry 33 includes a processor, such as a CPU (Central Processing Unit) and an MPU (Micro Processing Unit), and a memory, such as a ROM (Read Only Memory) and a RAM (Random Access Memory), as hardware resources. The gantry control circuitry 33 may be implemented by an ASIC or an FPGA (Field Programmable Gate Array), a CPLD (Complex Programmable Logic Device), or an SPLD (Simple Programmable Logic Device). The gantry control circuitry 33 of this embodiment achieves a light projector setting function 291 by executing a control program of the light projector 27.

By the light projector setting function 291, the gantry control circuitry 33 sets setting parameters that define an irradiation position of the visible light beam by the light projector 27, in accordance with the instructions from the user via the input circuitry 31. The setting parameter is referred to as the light projection parameter. The light projection parameters that define the irradiation position of the visible light beam include an irradiation angle of the visible light beam by the light projector 27, the position of a light source of the light projector 27, etc.

As shown in FIG. 1, the console 100 includes the processing circuitry 101, a display 103, input circuitry 105, and a memory 107.

The processing circuitry 101 includes a processor such as a CPU, an MPU, or a GPU (Graphics Processing Unit), etc. and a memory such as a ROM or a RAM, etc. as hardware resources. The processing circuitry 101 executes various programs to implement a preprocessing function 111, a reconstruction function 113, an image processing function 115, a cross-sectional shape estimation function 117-1, an SSDE calculation function 119, a correction parameter determination function 121, an imaging parameter determination function 123, and a system control function 125. The preprocessing function 111, the reconstruction function 113, the image processing function 115, the cross-sectional shape estimation function 117-1, the SSDE calculation function 119, the correction parameter determination function 121, the imaging parameter determination function 123, and the system control function 125 may be implemented on one substrate of the processing circuitry 101 or separately implemented on a plurality of substrates of the processing circuitry 101.

By the preprocessing function 111, the processing circuitry 101 performs preprocessing such as logarithmic conversion to raw data transmitted from the gantry 10. The preprocessed raw data is also referred to as projection data.

By the reconstruction function 113, the processing circuitry 101 generates a CT image representing a space distribution of CT values relating to the patient P based on the preprocessed raw data. The known image reconstruction algorithm, such as an FBP (Filtered Back Projection) method or a successive approximation reconstruction method, may be adopted.

By the image processing function 115, the processing circuitry 101 performs various image processing to a CT image reconstructed by the reconstruction function 113. For example, the processing circuitry 101 performs three-dimensional image processing, such as volume rendering, surface volume rendering, pixel value projection processing, MPR (Multi-Planer Reconstruction) processing, CPR (Curved MPR) processing, etc. to the CT image to generate a display image.

By the cross-sectional shape estimation function 117-1, the processing circuitry 101 estimates a shape index value relating to an imaged cross section of the patient P included in the CT imaging range, based on the positions of the visible light beams projected by the light projector 27 to the patient P. The shape index value is referred to as a cross-sectional shape index value. For example, the processing circuitry 101 applies the radiation position of the visible light beam to be projected on the patient P to a human body model resembling a three-dimensional shape of a human body, thereby estimating a cross-sectional shape index value relating to the imaged cross section corresponding to the radiation position of the visible light beam.

By the SSDE calculation function 119, the processing circuitry 101 calculates an SSDE (Size-Specific Dose Estimates) value based on the cross-sectional shape index value estimated by the cross-sectional shape estimation function 117-1 and a CTDI (Computed Tomography Dose Index) value measured in advance.

By the correction parameter determination function 121, the processing circuitry 101 determines correction parameters to correct the shape of the imaged cross section of the patient P, the cross-sectional shape index value of the cross section, and the SSDE value. The correction parameters according to the first embodiment include a correction parameter corresponding to the height of the table top (hereinafter referred to as the bed height correction parameter), and a correction parameter corresponding to a deviation of a dose value which has been actually measured from the SSDE value calculated by the SSDE calculation function 119 (hereinafter referred to as the deviation correction parameter).

By the imaging parameter determination function 123, the processing circuitry 101 determines a plurality of imaging parameters constituting imaging conditions for CT imaging. The imaging parameters include a tube voltage value, a tube current value, and a modulation parameter relating to a directional modulation of the tube current.

The processing circuitry 101 determines the modulation parameter based on the cross-sectional shape index value estimated by the cross-sectional shape estimation function 117-1.

By the system control function 125, the processing circuitry 101 integrally controls the X-ray computed tomography apparatus according to the present embodiment. Specifically, the processing circuitry 101 reads a control program stored in the memory 107, deploys the control program, and controls the respective units of the X-ray computed tomography apparatus in accordance with the deployed control program.

The display 103 displays various data, such as a CT image, etc. For the display 103, for example, a CRT display, a liquid crystal display, an organic EL display, an LED display, a plasma display, or any other display known in this technical field may be used as appropriate.

The input circuitry 105 accepts various instructions from the user. Specifically, the input circuitry 105 includes an input device and an input interface. The input device receives various instructions from the user. A keyboard, a mouse, various types of switches, a touch pad, a touch panel display, etc. can be used as the input device. The input interface supplies an output signal from the input device to the processing circuitry 101 via a bus. The input device of the input circuitry 105 may be computer equipment connected to the console 100 by wired or wireless connection and including the input device.

The memory 107 is a storage device, such as an HDD (Hard Disk Drive), an SSD (Solid State Drive), or an integrated circuit storage device, etc. which stores various types of information. The memory 107 may also be a driving device, etc. which reads and writes various information to and from portable storage media, such as a CD-ROM drive, a DVD drive, and a flash memory. For example, the memory 107 stores a control program, etc. relating to CT imaging according to the present embodiment.

FIG. 2 is a schematic view showing an appearance of the gantry 10 according to the first embodiment. FIG. 3 is a cross-sectional view including a Z axis of the gantry 10 shown in FIG. 2. The central axis of the rotation frame 11 is defined as a Z axis; an axis vertically perpendicular to the Z axis is defined as a Y axis; and an axis horizontally perpendicular to the Z axis is defined as an X axis. As shown in FIG. 2 and FIG. 3, the gantry 10 includes a gantry housing 40 with a substantially cylindrical bore 41. The gantry housing 40 houses a main frame 43 which serves as a fixed unit, and the rotation frame 11 which serves as a rotation unit. The main frame 43 supports the rotation frame 11 so that the rotation frame 11 can be continuously rotated around the Z axis via a bearing. The X-ray tube 13, the X-ray detector 15, and the data acquisition circuitry 19, which are not shown in FIG. 2 and FIG. 3, are mounted on the rotation frame 11. The light projector 27 is mounted on the rotation frame 11 in such a manner that a visible light beam projected from the light projector 27 can be directed toward the bore 41. The light projector 27 projects visible light beams which render the reference lines of the CT imaging range directly visible. The reference lines of the CT imaging range include central lines relating to X, Y and Z directions of the CT imaging range, and frame lines constituting an outer frame of the CT imaging range. The reference lines of the CT imaging range are not limited to the above, but may be any lines which are useful for positioning of the imaging target area of the patient P in the CT imaging range.

As shown in FIG. 2 and FIG. 3, a gap 47 is provided to allow passage of the visible light beams projected from the light projector 27 and the X-rays generated from the X-ray tube 13 (not shown) on a part of the inner wall of the gantry housing 40 that faces the bore 41. Since the light projector 27 and the X-ray tube 13 are mounted on the rotation frame 11, the gap 47 is provided in the entire circumference of the inner wall around the Z axis. A transmission film 45 is attached to cover the gap 47. The visible light beams projected from the light projector 27 and the X-rays generated from the X-ray tube 13 transmit through the transmission film 45. For example, the transmission film 45 is formed as a transparent or translucent film made of polyester.

To specifically explain the embodiment, it is assumed that visible light beams projected from the light projector 27 represent frame lines constituting an outer frame of the CT imaging range.

FIG. 4 is a diagram showing an example of visible light beams Lz and Lx which represent frame lines constituting the outer frame of the CT imaging range. As shown in FIG. 4, the visible light beams Lz represent an outer frame of the imaging range in the Z direction. More specifically, the visible light beams Lz include a light beam Lz1 on a front side (for example, the head side of the patient P) of the Z axis and a light beam Lz2 on a back side (for example, the foot side of the patient P). The relationship between the direction of the patient P and the direction of the Z axis is not limited to this; the front side of the Z axis may be the foot side of the patient P, and the back side of the Z axis may be the head side of the patient P. The radiation position of the light beam Lz1 and the radiation position of the light beam Lz2 are adjustable independently of each other along the Z axis. The visible light beams Lx include a light beam Lx1 on a left side of the X axis and a light beam Lx2 on a right side. The radiation position of the light beam Lx1 and the radiation position of the light beam Lx2 are adjustable independently of each other along the X axis. For example, the user performs adjustment of the radiation positions of the visible light beams Lz1, Lz2, Lx1, and Lx2 by operating the input circuitry 31 or 105. The gantry control circuitry 33 sets light projection parameters to apply the visible light beams Lz1, Lz2, Lx1, and Lx2 to the radiation positions in accordance with the adjustment. In other words, the gantry control circuitry 33 sets positions of the light source of the light projector 27 or irradiation angles of the light beams so that the visible light beams Lz1, Lz2, Lx1, and Lx2 can be applied to the radiation positions in accordance with the adjustment. Then, the gantry control circuitry 33 moves the light source of the light projector 27 to the set positions or inclines the light source of the light projector 27 at the irradiation angles. As a result, the visible light beams Lz1, Lz2, Lx1, and Lx2 can be applied to the radiation positions in accordance with the light projection parameters.

FIG. 2 and FIG. 3 show an example in which two light projectors 271 are mounted on the rotation frame 11. However, the X-ray computed tomography apparatus of the embodiment is not limited to this. Any number of light projectors 27 may be mounted on the rotation frame 11. Should the light projector 27 not need to be rotated around the rotation axis Z, it may be mounted on a component other than the rotation frame 11 of the gantry 10, for example, to the main frame 43 or the gantry housing 40.

Figure 5:
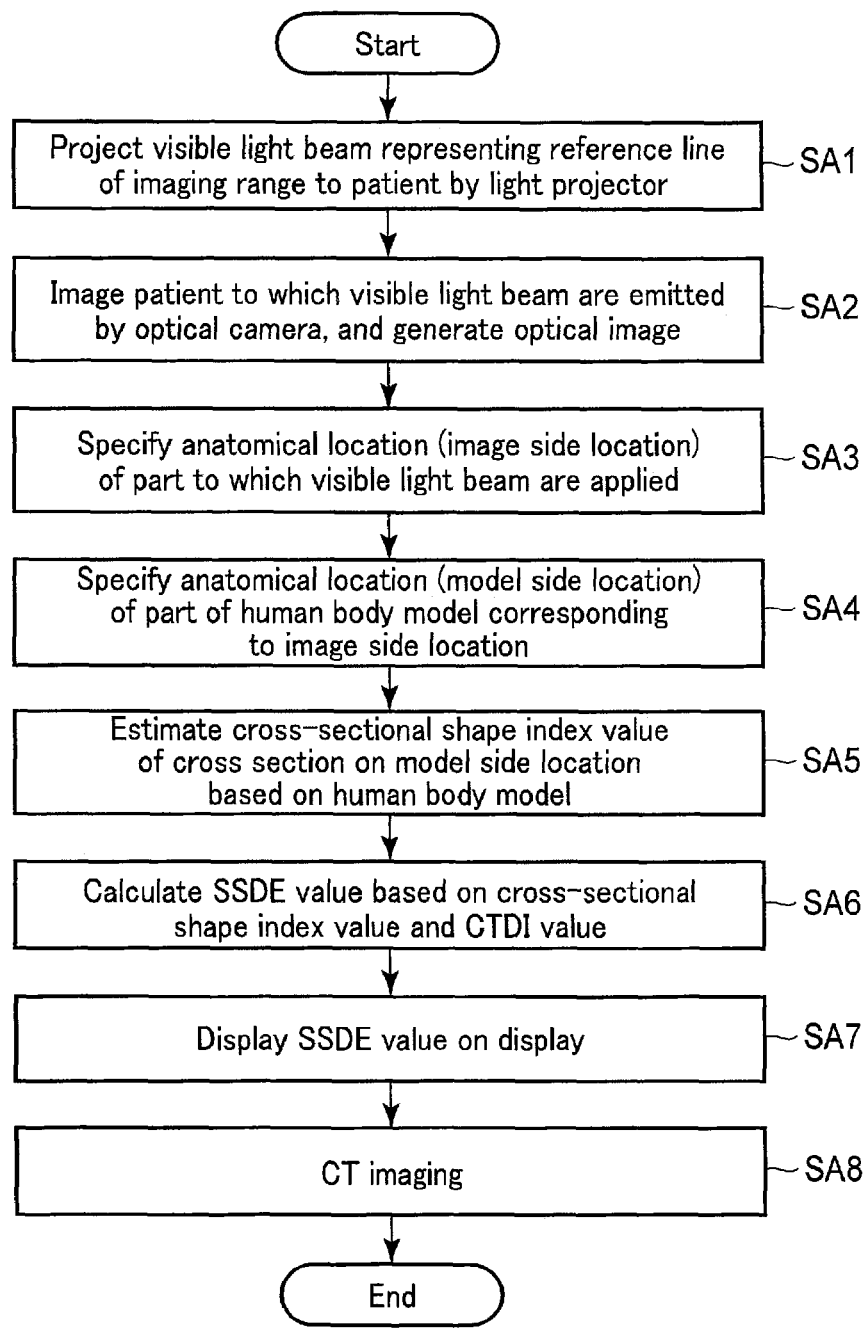
FIG. 5 is a flowchart illustrating a typical operation of the X-ray computed tomography apparatus, performed by execution of a system control function of processing circuitry according to the first embodiment.

FIG. 5 is a flowchart illustrating a typical operation of the X-ray computed tomography apparatus, performed by execution of the system control function 125 of the processing circuitry 101 according to the first embodiment. First, as shown in FIG. 5, the processing circuitry 101 directs the gantry control circuitry 33 to perform radiation of the visible light beams (step SA1). In step SA1, the gantry control circuitry 33 directs the light projector 27 to project the visible light beams representing the reference lines of the CT imaging range to the patient P. For example, the user, such as a healthcare professional, performs operations with the input circuitry 31 to include the imaging target area of the patient P in the CT imaging range, thereby adjusting the height of the table top 231 of the bed 23 (hereinafter referred to as the bed height). At this time, the light projector 27 projects visible light beams representing an outer frame of the CT imaging range as the visible light beams representing the reference lines of the CT imaging range. The radiation positions of the visible light beams can be adjusted at desired positions by the user via the input circuitry 31 or 105. The light projection parameters corresponding to the radiation positions of the visible light beams are transmitted from the gantry control circuitry 33 to the console 100 and stored in the memory 107.

After step SA1, the processing circuitry 101 directs the optical camera 29 to perform optical imaging (step SA2). In step SA2, the optical camera 29 optically images the patient P irradiated with the visible light beams, and generates an optical image (step SA2). In the optical image, for example, RGB values are allocated to the respective pixels. At an optical imaging time, the center of the height in the imaging range of the patient P need not coincide with the height of the isocenter. The generated optical image is transmitted to the console 100 and stored in the memory 107. At this time, the value of the bed height is stored in association with the optical image.

Figure 6:
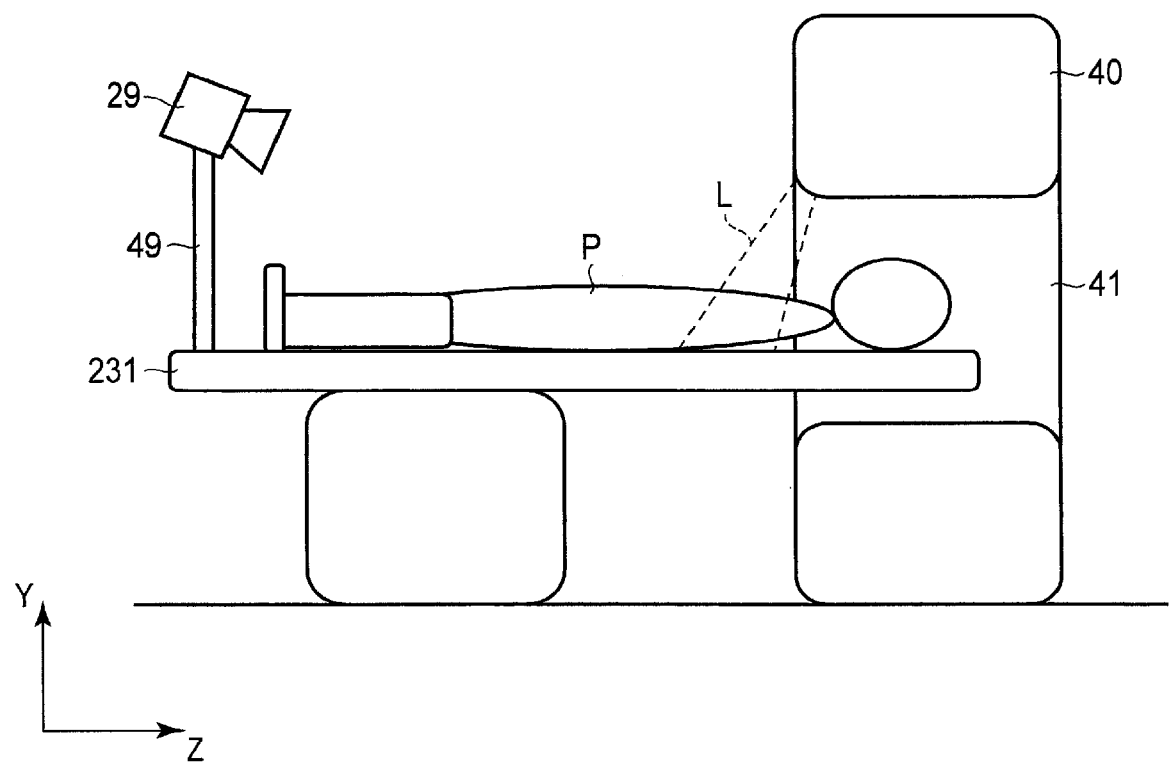
FIG. 6 is a schematic view showing a placement of an optical camera shown in FIG. 1.

FIG. 6 is a schematic view showing a placement of the optical camera 29. As shown in FIG. 6, at a positioning time, the visible light beams L representing an outer frame of the CT imaging range are projected from the light projector 27 toward the patient P placed in the table top 231 of the bed 23. The optical camera 29 is mounted on an end of the table top 231, opposite to the gantry housing 40 via a support bar 49. The optical camera 29 is attached to a height and at an angle so that the patient P irradiated with the visible light beams L projected from the light projector 27 is covered by the optical imaging range. For example, the optical camera 29 is not necessarily mounted on the table top 231 via the support bar 49, but may be mounted on the gantry 10, or a ceiling or side wall of the examination room.

After step SA2, the processing circuitry 101 executes the cross-sectional shape estimation function 117-1. By the cross-sectional shape estimation function 117-1, first, the processing circuitry 101 subjects the optical image generated by the optical camera 29 to image processing, and specifies an anatomical location of the part irradiated with the visible light beams (step SA3). In the embodiment, the anatomical location does not denote the coordinates of the optical image, but denotes a location in the anatomical site irradiated with the visible light beams. For example, the anatomical location is defined by a position relative to a reference point of the imaging target area. The specified anatomical location is hereinafter referred to as the image side location.

Figure 7:
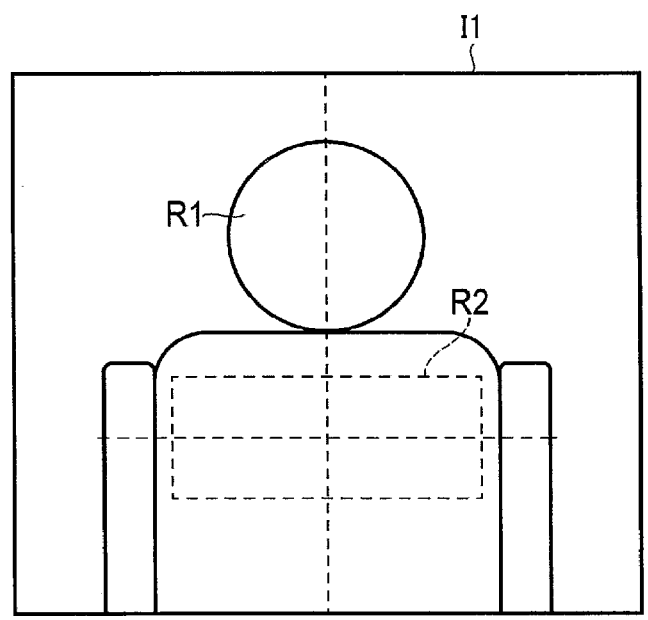
FIG. 7 is a schematic view showing an example of an optical image generated by the optical camera shown in FIG. 6.

FIG. 7 is a schematic view showing an example of an optical image I1 generated by the optical camera 29. As shown in FIG. 7, the optical image I1 includes an image region R1 relating to the patient P (hereinafter referred to as the patient region), and an image region R2 relating to visible light beams (hereinafter referred to as the visible light beam region). The processing circuitry 101 subjects the optical image I1 to threshold processing or the like, and specifies the visible light beam region R2. Then, by image recognition processing or the like, the processing circuitry 101 specifies as the image side location an anatomical location in the patient region R1 where the visible light beam region R2 is present. For example, in the case shown in FIG. 7, the imaging target area is a chest region. In this case, a part of the chest region is specified as the image side location R2 by the image processing mentioned above. The image side location may be specified at a location designated by the user via the input circuitry 105. Information on the imaging target area may be specified by the image recognition processing for the optical image I1, or may be acquired from the imaging conditions.

After executing step SA3, the processing circuitry 101 specifies an anatomical location in the human body model that corresponds to the image side location specified in step SA3 (step SA4). The specified anatomical location is referred to as the model side location. Data on the human body model is stored in the memory 107.

FIG. 8 is an example of a human body model MD. The human body model MD is data on a human body model resembling a three-dimensional shape of a human body. The human body model MD reflects not only the outer shape of a human body but also internal structures such as internal organs. For example, if the partial region R2 of the chest region is specified as the image side location as shown in FIG. 7, a partial region of the human body model that anatomically corresponds to the chest region R2 is specified as a model side location R2'. It is assumed that the coordinate system of the human body model MD and the coordinate system of the optical image I1 are associated with each other in advance.

After executing step SA4, the processing circuitry 101 estimates a cross-sectional shape index value relating to the cross section at the model side location specified in step SA4 (step SA5). In step SA5, the processing circuitry 101 first sets an estimation target cross section included in the model side location. The estimation target cross section is determined at discretion from a plurality of imaged cross sections included in the model side location. The imaged cross sections are assumed to be cross sections in the CT imaging range of the patient P.

Once the estimation target cross section is set, the processing circuitry 101 estimates a cross-sectional shape index value in the cross section. Specifically, the cross-sectional shape index value is defined by a length in an AP (Anterior-Posterior) direction (hereinafter referred to as the AP length) of the human body model, a length in an LR (Left-Right) direction (hereinafter referred to as the LR length), the total of the AP length and the LR length, an effective diameter, a water equivalent diameter, etc.

FIG. 9 is a schematic view of an example of an imaged cross section of the human body model MD. In FIG. 9, "A" represents an anterior side, "P" represents a posterior side, "L" represents a left side, and "R" represents a right side of the patient. For example, if the cross-sectional shape of the human body model is expressed by a water equivalent length (a dimension obtained by converting a length of an X-ray transmission path to a length of a water transmission path), the diameter of the cross section of the human body model is equal to the water equivalent diameter. In this case, the processing circuitry 101 can estimate a water equivalent diameter of the patient P by measuring the diameter of the cross section of the human body model. On the other hand, if the cross-sectional shape of the human body model is expressed by an actual path length, the AP length of the patient P can be estimated by measuring the length in the AP direction of the cross section of the human body model, and the LR length of the patient P can be estimated by measuring the length in the LR direction of the cross section of the human body model. The total length of the patient P can be estimated by adding the AP length and the LR length, and the effective diameter of the patient P can be estimated from the square root of the product of the AP length and the LR length.

The processing circuitry 101 can correct the estimated cross-sectional shape index value based on the bed height correction parameter. The correction parameter in accordance with the bed height is determined by the correction parameter determination function 121 of the processing circuitry 101.

Figure 10:
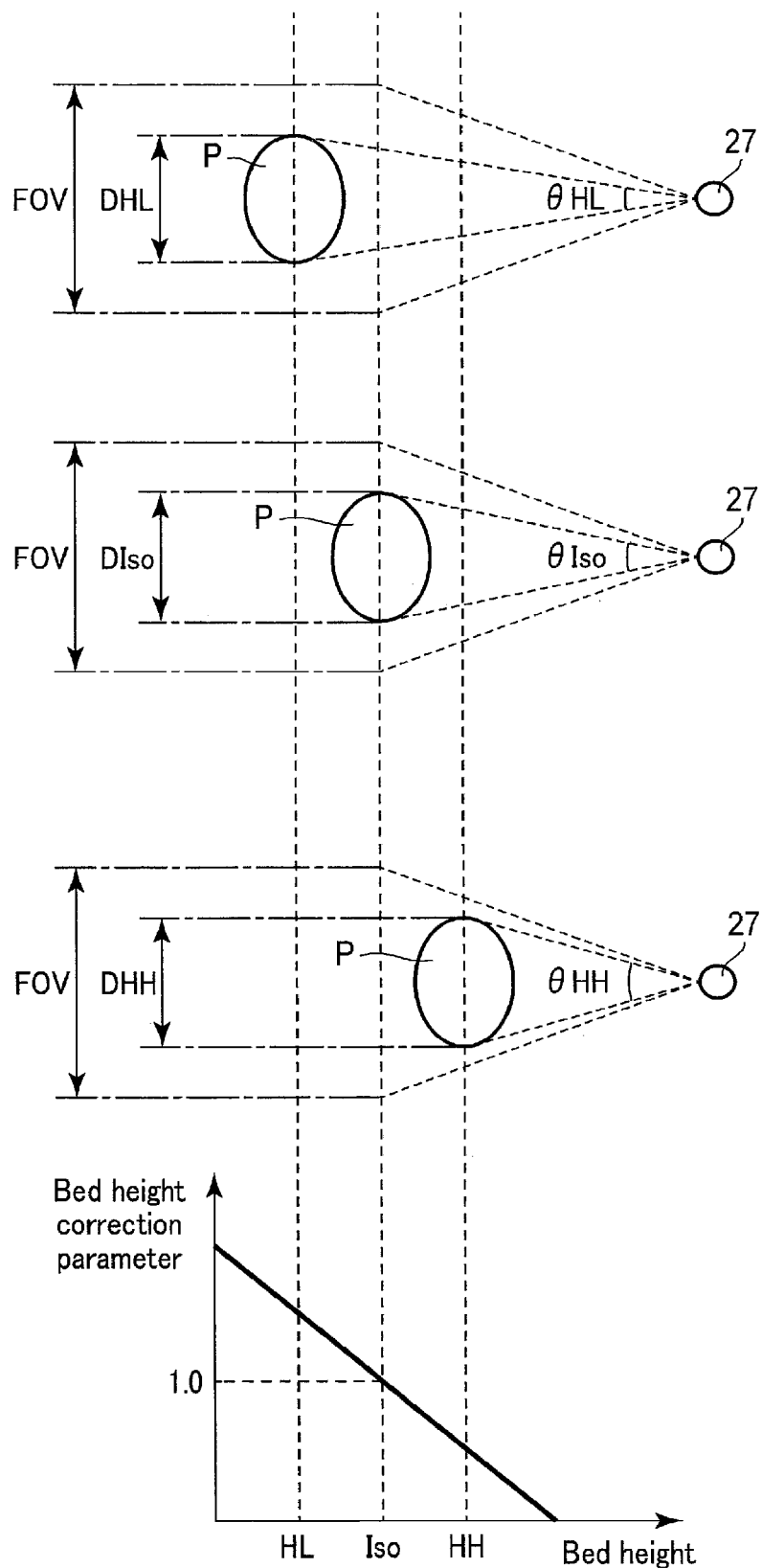
FIG. 10 is a diagram for explaining a bed height correction parameter determined by a correction parameter determination function of the processing circuitry shown in FIG. 1.

FIG. 10 is a diagram for explaining a bed height correction parameter determined by the correction parameter determination function 121 of the processing circuitry 101. As shown in FIG. 10, the ordinate defines the bed height correction parameter, and the abscissa defines the bed height. The bed height Iso is defined as a height of the table top 231 when the center in the Y axis direction of the patient P lying on the table top 231 is located at the isocenter. A bed height HL is lower than the height Iso, and a bed height HH is higher than the height Iso. As shown in FIG. 10, the higher the bed height, the shorter the distance between the patient P and the light projector 27, and therefore, the dimension D of the patient P relative to the CT imaging range (FOV), namely the geometric magnification ratio, is increased. For example, the geometric magnification ratio DHL/FOV of the dimension DHL of the patient P to the FOV at the bed height HL is smaller than the geometric magnification ratio DHH/FOV of the dimension DHH of the patient P to the FOV at the bed height HH. In other words, the angle of divergence θHL of the region projected on the patient P at the bed height HL is smaller than the angle of divergence θHH of the region projected on the patient P at the bed height HH. Therefore, as the geometric magnification ratio of the patient P is increased, the cross-sectional shape index value is overestimated relative to the cross-sectional shape index value at the isocenter. Conversely, as the geometric magnification ratio of the patient P is decreased, the cross-sectional shape index value is underestimated relative to the cross-sectional shape index value at the isocenter. Thus, it is necessary to correct the cross-sectional shape index value at a discretionary bed height to the cross-sectional shape index value at the isocenter.

As shown in FIG. 10, there is a linear relationship between the bed height correction parameter and the bed height; specifically, the bed height correction parameter has a smaller value as the bed height is increased. The correction parameter at the height Iso is set to "1". The processing circuitry 101 stores a table (LUT: Look Up Tale) that defines the relationship between the bed height and the bed height correction parameter shown in FIG. 10. In the following description, the table is referred to as the bed height correction table. The processing circuitry 101 acquires a bed height value at the optical imaging time for the patient P by the optical camera 29 from the gantry 10, and determines a bed height correction parameter from the bed height correction table based on the acquired bed height value. By the cross-sectional shape estimation function 117-1, the processing circuitry 101 estimates a cross-sectional shape index value by multiplying the determined bed height correction parameter by a provisionally determined cross-sectional shape index value.

After execution of step SA5, the cross-sectional shape estimation function 117-1 is ended.

Next, the processing circuitry 101 executes the SSDE calculation function 119 (step SA6). In step SA6, the processing circuitry 101 calculates an SSDE value based on the water equivalent diameter and the CTDI value measured in advance. More specifically, the processing circuitry 101 determines a conversion factor from the water equivalent diameter, and calculates the SSDE value by multiplying the determined conversion factor by the CTDI value. For example, the processing circuitry 101 stores a table (LUT: Look Up Tale) that associates the water equivalent diameter with the conversion factor. The table is referred to as the water equivalent diameter/conversion factor table. The processing circuitry 101 searches the water equivalent diameter/ conversion factor table using the water equivalent diameter calculated in step SA5 as a search key, and determines the conversion factor associated with the water equivalent diameter. The CTDI value is measured by CT imaging of a phantom for CTDI measurement in a geometry for the CTDI measurement. The CTDI value is stored in the memory 107.

The SSDE value may be calculated for each of all imaged cross sections included in the model side location. In this case, the processing circuitry 101 calculates an average value, central value, maximum value, or minimum value of a plurality of SSDE values relating to a plurality of imaged cross sections as the SSDE value of the entire CT imaging range.

After step SA6, the processing circuitry 101 directs the display 103 to display the SSDE value calculated in the step SA6 (step SA7). Specifically, the display 103 may display the SSDE value of each imaged cross section or the SSDE value of the entire CT imaging range. The user checks the displayed SSDE value, and if the SSDE value is determined to be unacceptable, the user reviews the imaging conditions or the like. If the SSDE value is determined to be acceptable, the user inputs imaging instructions via the input circuitry 31 or 105.

After step SA7, once the user inputs imaging instructions via the input circuitry 31 or 105, the processing circuitry 101 directs the gantry control circuitry 33 to start imaging (step SA8). The gantry control circuitry 33, which has been instructed to start imaging, synchronously controls the X-ray high voltage device 17, the data acquisition circuitry 19, the rotation actuator 21, the bed actuator 25, etc. in accordance with imaging conditions, to perform CT imaging for the patient P.

The operation flow of the X-ray computed tomography apparatus according to the first embodiment is completed with the above explanations.

A plurality of human body models of different physical types may be stored in the memory 107, and the processing circuitry 101 may choose one of the human body models that is similar to the body shape of the patient P. For example, the human body model may be chosen in accordance with an instruction given by the user via the input circuitry 105. Alternatively, the human body model that is closest to the body shape of the patient P may be chosen based on patient information, such as the age, the sex, and anthropometric measurements. The anthropometric measurements in this embodiment include any measurements concerning the body shape of the patient, such as the body height, the weight, and the chest circumference. The processing circuitry 101 may correct the shape of the human body model to conform to the body shape of the patient P based on the patient information, such as the age, the sex, and anthropometric measurements. Thus, by using the human body model approximate to the body shape of the patient P, the estimation target cross section is more approximate to the actual cross section of the patient P. Accordingly, the accuracy of the estimation of the cross-sectional shape is improved, and the accuracies of the cross-sectional shape index value and the SSDE value are also improved.

The cross-sectional shape index value is applicable to various purposes, not only the calculation of the SSDE value. For example, by the imaging parameter determination function 123, the processing circuitry 101 can determine parameters that define a directional modulation of the tube current (hereinafter referred to as the tube current modulation parameters) based on the cross-sectional shape index value estimated by the cross-sectional shape estimation function 117-1. Specifically, the processing circuitry 101 determines a ratio of a tube current value in the AP direction to a reference value of the tube current, and a ratio of a tube current value in the LR direction to the reference value of the tube current in accordance with the ratio of the water equivalent diameter in the AP direction to the water equivalent diameter in the LR direction. The ratios are set as the tube current modulation parameters. The tube current modulation parameters may be the tube current value in the AP direction and the tube current value in the LR direction.

As described above, according to the first embodiment, the tube current modulation parameters can be determined based on the cross-sectional shape index value estimated in accordance with the radiation positions of the visible light beams projected from the light projector 27, and not a cross-sectional shape index value estimated in accordance with a positioning image. Therefore, the exposure to radiation of the patient P can be reduced.

Furthermore, the processing circuitry 101 may determine the correction parameter of the SSDE value in accordance with a difference between the SSDE value and the dose value which has been actually measured by the correction parameter determination function 121. The processing will be described in detail below. When the CT imaging is performed in step SA8, the processing circuitry 101 measures the actual dose value of the patient P. The memory 107 stores the dose value which has been actually measured and the SSDE value relating to the patient P in association with each other. The memory 107 stores the dose value which has been actually measured and the SSDE value in association with each other for each of a plurality of patients. By the correction parameter determination function 121, the processing circuitry 101 calculates a difference value between the dose value which has been actually measured and the SSDE value stored in the memory 107, analyzes the calculated difference value, and determines a correction parameter (hereinafter referred to as the SSDE correction parameter) to approximate the SSDE value calculated by the SSDE calculation function 119 to the does value which has been actually measured. The SSDE correction parameter may be a parameter common to all patients P, or may be a parameter determined for each classification of patients P, such as the body shape. When the SSDE correction parameter is determined, the processing circuitry 101 estimates the SSDE value based on the cross-sectional shape index value, the CTDI value, and the SSDE correction parameter in step SA6. As a result, the accuracy of estimating the SSDE value can be further improved.

In the above example, only one optical camera 29 is placed. However, the present embodiment is not limited to this. A plurality of optical cameras 29 may be placed. For example, one optical camera 29 to optically image the anterior side of the patient P and another optical camera 29 to optical image a side of the patient P may be placed. The processing circuitry 101 can determine the anatomical location in the CT imaging range based on optical images in a plurality of directions, thereby improving the accuracy of estimation of the anatomical location and also the accuracies of the cross-sectional shape index value and estimation of the SSDE value.

The optical camera 29 may be mounted on the rotation frame 11. By mounting the optical camera 29 on the rotation frame 11, an optical image of the entire circumference of the patient P can be generated by the single optical camera 29. By determining the anatomical location of the CT imaging range based on the optical image of the entire circumference, the processing circuitry 101 can improve the estimation accuracy of the anatomical location, and accordingly the estimation accuracies of the cross-sectional shape index value and the SSDE value.

If the body shape of the patient P is very large, the patient may be too close to the light projector 27. In this case, it is difficult to make the radiation positions of the visible light beams from the light projector 27 coincide with the CT imaging range. For example, triggered by an alert instruction input by the user via the input circuitry 31 or 105, the processing circuitry 101 generates an alert indicating that a cross-sectional shape index value cannot be estimated. The generation of the alert may be an output of an alert sound by a speaker, a display of an alert message in the display 103, etc. Accordingly, the user can switch the estimation to the estimation of the SSDE value based on the positioning image.

With the configuration described above, according to the first embodiment, the cross-sectional shape index value can be estimated on the basis of the human body model and the optical image of the patient P irradiated with the visible light beams projected from the light projector 27 at the time of positioning the patient P. In other words, when estimating the cross-sectional shape index value, the X-ray computed tomography apparatus according to the first embodiment does not require imaging for positioning. Therefore, the X-ray computed tomography apparatus according to the first embodiment can estimate the cross-sectional shape index value with less exposure to radiation of the patient P as compared to the case in which imaging for positioning is performed.

Second Embodiment

The X-ray computed tomography apparatus of the first embodiment described above is equipped with the optical camera 29. However, the present embodiment is not limited to this. In the second embodiment, the estimation of the cross-sectional shape index value and the calculation of the SSDE value are performed without using the optical camera 29. Details of the second embodiment will be described below. In the description below, structural elements with substantially the same functions as those of the first embodiment will be denoted by the same reference symbols, and a repetitive description will be given only where necessary.

FIG. 11 is a diagram showing a configuration of the X-ray computed tomography apparatus according to the second embodiment. As shown in FIG. 11, the X-ray computed tomography apparatus of the second embodiment does not include an optical camera. By a cross-sectional shape estimation function 117-2, processing circuitry 101 of the second embodiment specifies radiation positions of visible light beams projected to a patient P from a light projector 27 based on projection parameters, and estimates a cross-sectional shape index value of a cross section corresponding to the specified radiation positions using a human body model.

Figure 12:
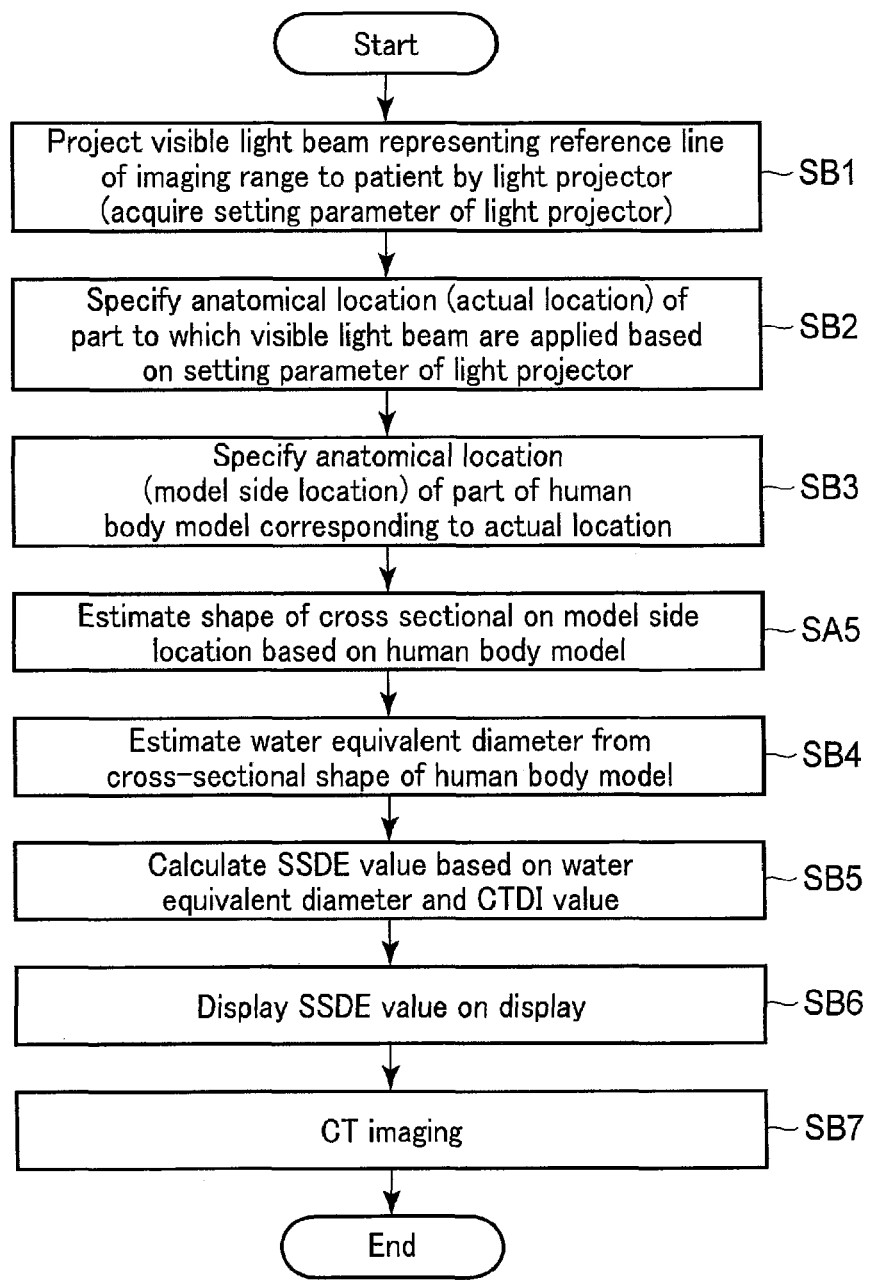
FIG. 12 is a flowchart illustrating a typical operation of the X-ray computed tomography apparatus, performed by execution of a system control function of processing circuitry according to the second embodiment.

FIG. 12 is a flowchart illustrating a typical operation of the X-ray computed tomography apparatus, performed by execution of a system control function 125 of the processing circuitry 101 according to the second embodiment.

As shown in FIG. 12, first, the processing circuitry 101 directs gantry control circuitry 33 to perform radiation of visible light beams (step SB1). In step SB1, in the same manner as in step SA1 of the first embodiment, the gantry control circuitry 33 directs the light projector 27 to project the visible light beams to the patient P (step SB1). In the former step of the radiation of the visible light beams, projection parameters relating to the radiation positions of the visible light beams are set in the same manner as in step SA1. The light projection parameters are transmitted to a console 100 and stored in a memory 107.

After step SB1, the processing circuitry 101 executes the cross-sectional shape estimation function 117-2. By the cross-sectional shape estimation function 117-2, first, the processing circuitry 101 specifies an anatomical location of the part irradiated with the visible light beams based on the light projection parameters acquires in step SB1 (step SB2). Specifically, the processing circuitry 101 specifies anatomical locations irradiated with the visible light beams based on an imaging target area and the light projection parameters (the position of a light source and an irradiation angle of the light projector 27) included in imaging conditions. In addition to the imaging target area and the light projection parameters, an anatomical location may be specified utilizing a Z-axis coordinate and a Y-axis coordinate of a table top 231.

After executing step SB2, the processing circuitry 101 specifies an anatomical location in the human body model that corresponds to the actual location specified in step SB2 (step SB3). Specifically, the processing circuitry 101 specifies the anatomical location in the human body model in the same manner as in step SA4 of the first embodiment.

After executing step SB3, the processing circuitry 101 estimates a water equivalent diameter in the cross section at a model side location specified in step SB3 (step SB4). Specifically, the processing circuitry 101 estimates the water equivalent diameter in the same manner as in step SA5 of the first embodiment.

After step SB4, the processing circuitry 101 calculates an SSDE value based on the water equivalent diameter estimated in step SB4 and the CTDI value measured in advance (Step SB5). Specifically, the processing circuitry 101 calculates the SSDE value in the same manner as in step SA6 of the first embodiment.

After step SB5, the processing circuitry 101 directs the display 103 to display the SSDE value calculated in the step SB5 (step SB6). Specifically, the display 103 displays the SSDE value in the same manner as in step SA7 of the first embodiment. The user checks the displayed SSDE value, and if the SSDE value is determined to be unacceptable, reviews the imaging conditions or the like. If the SSDE value is determined to be acceptable, the user inputs imaging instructions via the input circuitry 31 or 105.

After step SB6, once the user inputs imaging instructions via the input circuitry 31 or 105, the processing circuitry 101 directs the gantry control circuitry 33 to start imaging (step SB7). The gantry control circuitry 33, which has been instructed to start imaging, synchronously controls the X-ray high voltage device 17, the data acquisition circuitry 19, the rotation actuator 21, the bed actuator 25, etc. in accordance with imaging conditions, to perform CT imaging for the patient P.

The operation flow of the X-ray computed tomography apparatus according to the second embodiment is completed with the above explanations.

With the configuration described above, according to the second embodiment, the cross-sectional shape index value can be estimated on the basis of the human body model and the projection light parameters of the light projector 27 at the time of positioning the patient P. In other words, when estimating the cross-sectional shape index value, the X-ray computed tomography apparatus according to the second embodiment does not require imaging for positioning. Therefore, the X-ray computed tomography apparatus according to the second embodiment can estimate the cross-sectional shape index value with less exposure to radiation of the patient P as compared to the case in which imaging for positioning is performed. Since the second embodiment does not use an optical camera, it can estimate the cross-sectional shape index value via a simpler apparatus design as compared to the first embodiment. In other words, since the first embodiment uses the optical camera, it can estimate a cross section and further a cross-sectional shape index value more accurately as compared to the second embodiment.

Third Embodiment

In the X-ray computed tomography apparatuses according to the first and second embodiments, the estimation of the cross-sectional shape index value and the calculation of the SSDE value are performed using the human body model. However, the present embodiment is not limited to this. The third embodiment performs estimation of a cross-sectional shape index value and calculation of an SSDE value without using a human body model. Details of the third embodiment will be described below. In the description below, structural elements with substantially the same functions as those of the first and second embodiments will be denoted by the same reference symbols, and a repetitive description will be given only where necessary.

Figure 13:
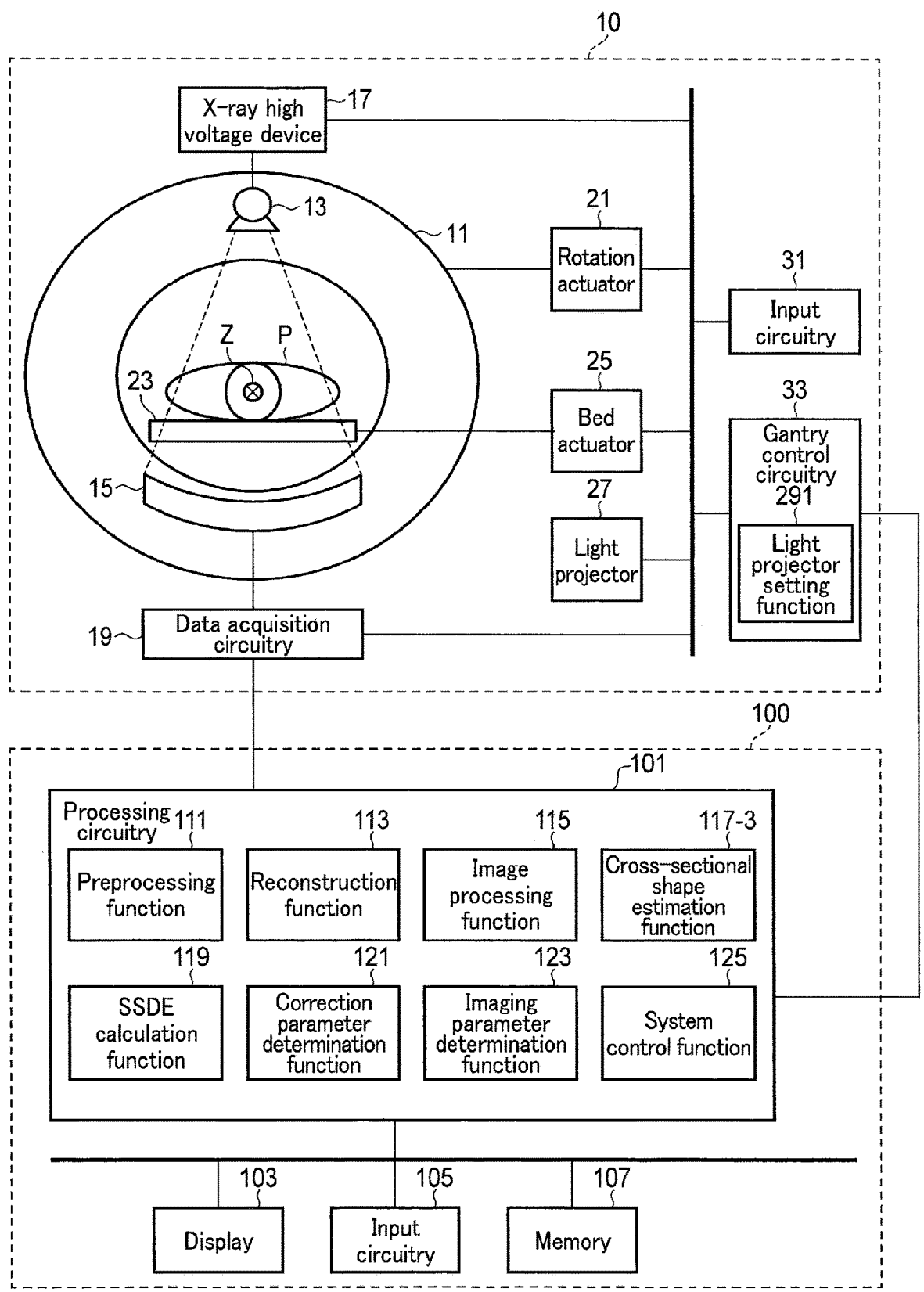
FIG. 13 is a diagram showing a configuration of an X-ray computed tomography apparatus according to a third embodiment.

FIG. 13 is a diagram showing a configuration of an X-ray computed tomography apparatus according to the third embodiment. As shown in FIG. 13, the processing circuitry 101 of the third embodiment executes a cross-sectional shape estimation function 117-3. By the cross-sectional shape estimation function 117-3, the processing circuitry 101 estimates across-sectional shape index value based on light projection parameters of a light projector 27 in two or more directions.

Figure 14:
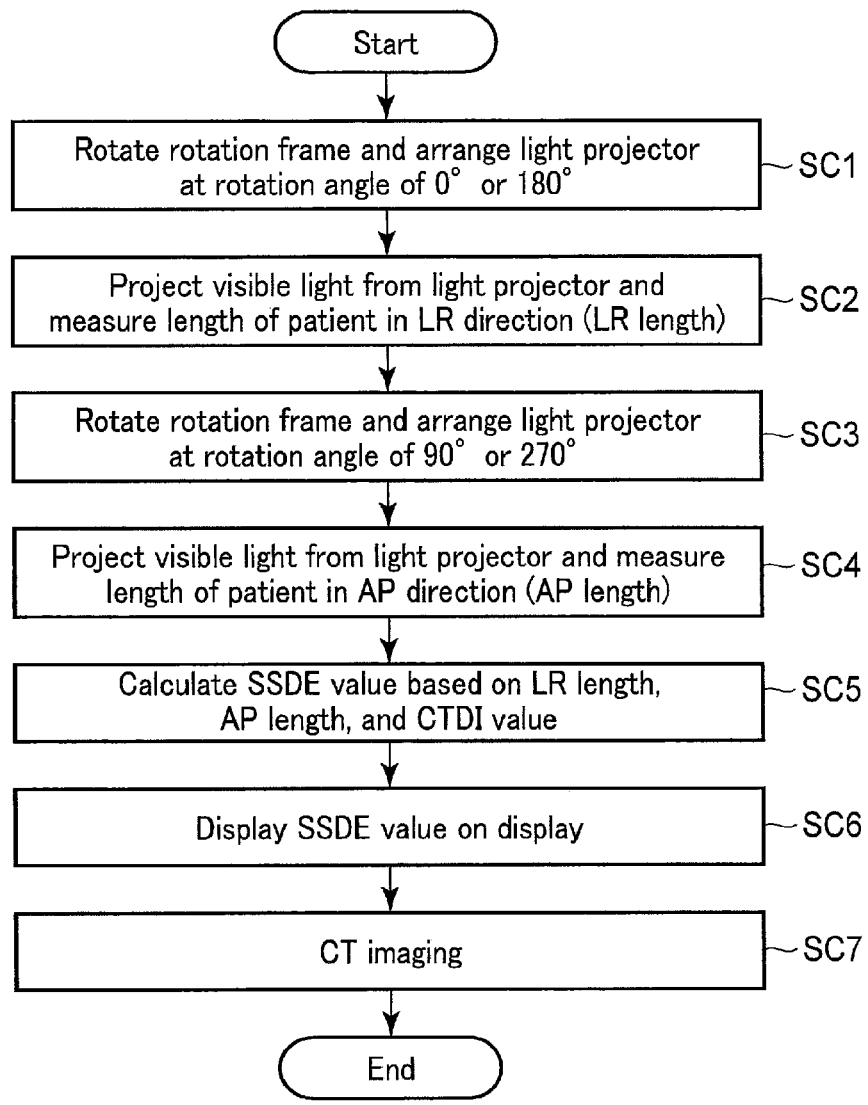
FIG. 14 is a flowchart illustrating a typical operation of the X-ray computed tomography apparatus, performed by execution of a system control function of processing circuitry according to the third embodiment.

FIG. 14 is a flowchart illustrating a typical operation of the X-ray computed tomography apparatus, performed by execution of the system control function 125 of the processing circuitry 101 according to the third embodiment. As shown in FIG. 14, first, the processing circuitry 101 executes the cross-sectional shape estimation function 117-3 in steps SC1 through SC4.

Figure 15:
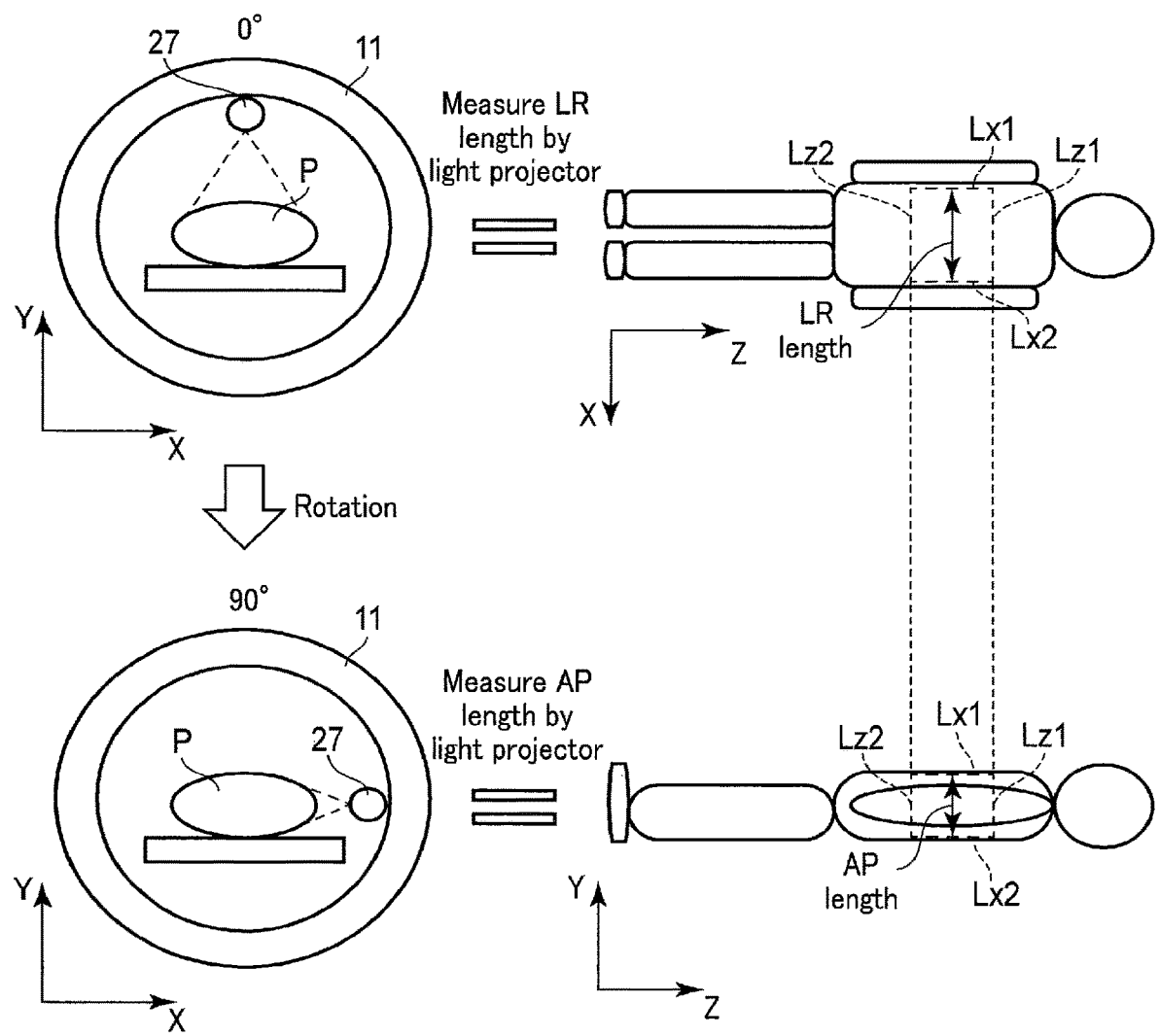
FIG. 15 is a schematic diagram illustrating a cross-sectional shape estimation function executed by the processing circuitry in steps SC1-SC4 in FIG. 14.

FIG. 15 is a schematic diagram illustrating a cross-sectional shape estimation function 117-3 executed by the processing circuitry 101 in steps SC1 through SC4.

As shown in FIG. 14 and FIG. 15, the processing circuitry 101 directs the gantry control circuitry 33 to rotate a rotation frame 11. The gantry control circuitry 33, first, controls a rotation actuator 21 to arrange the light projector 27 at a rotation angle of 0° or 180° (step SC1).

After step SC1, the processing circuitry 101 measures an LR length of a patient P based on the light projection parameters of the light projector 27 (step SC2). First, the user inputs a light projection start instruction via input circuitry 31. Upon receipt of the light projection start instruction, the gantry control circuitry 33 directs the light projector 27 to project visible light beams Lz1, Lz2, Lx1, and Lx2 to the patient P. Next, in accordance with the instruction by the user via the input circuitry 31, the gantry control circuitry 33 adjusts the distance between the visible light beams Lx1 and Lx2 in the LR direction to coincide with the CT imaging range in the LR direction of the patient P. When the adjustment is completed, the user inputs an adjustment completion instruction via the input circuitry 31.

The processing circuitry 101 estimates the LR length based on the light projection parameters at the time of the adjustment completion instruction and a geometry between the light projector 27 and the patient P or a table top 231. Specifically, the processing circuitry 101 measures an angle between the visible light beam Lx1 and the visible light beam Lx2 (hereinafter referred to as an interbeam angle) based on the irradiation angle of the visible light beam Lx1 and the irradiation angle of the visible light beam Lx2 at a rotation angle of 0°, and estimates a distance between the visible light beam Lx1 and the visible light beam Lx2 based on the interbeam angle and a bed height. The distance is set as the LR length. Alternatively, the processing circuitry 101 may measure a distance between the visible light beam Lx1 and the visible light beam Lx2 (hereinafter referred to as an interbeam distance) based on the light source position of the light projector 27 corresponding to the irradiation position of the visible light beam Lx1 and the light source position of the light projector 27 corresponding to the irradiation position of the visible light beam Lx2 at a rotation angle of 0°, and may estimate an LR length based on the interbeam distance and a bed height. The processing circuitry 101 may estimate the LR length based on a predicted value of the LR length of the patient P in addition to the interbeam angle or the interbeam distance and the bed height. Furthermore, the processing circuitry 101 may estimate the LR length using a distance between the light projector 27 and the patient P or the table top 231. Upon receipt of the adjustment completion instruction, the gantry control circuitry 33 transmits the LR length to a console 100, and a memory 107 stores the LR length.

After step SC2, the gantry control circuitry 33 controls a rotation actuator 21 to arrange the light projector 27 at a rotation angle of 90° or 270° (step SC3).

After step SC3, the processing circuitry 101 measures an AP length of the patient P based on the light projection parameters of the light projector 27 (step SC4). First, the user inputs a light projection start instruction via the input circuitry 31. Upon receipt of the light projection start instruction, the gantry control circuitry 33 directs the light projector 27 to project visible light beams Lz1, Lz2, Lx1, and Lx2 to the patient P. Next, in accordance with the instruction by the user via the input circuitry 31, the gantry control circuitry 33 adjusts the distance between the visible light beams Lx1 and Lx2 in the AP direction to coincide with the CT imaging range in the AP direction of the patient P. When the adjustment is completed, the user inputs an adjustment completion instruction via the input circuitry 31.

The processing circuitry 101 estimates the AP length based on the light projection parameters at the time of the adjustment completion instruction and a geometry between the light projector 27 and the patient P or the table top 231. Specifically, the processing circuitry 101 measures the interbeam angle based on the irradiation angle of the visible light beam Lx1 and the irradiation angle of the visible light beam Lx2 at a rotation angle of 90°, and estimates the distance between the visible light beam Lx1 and the visible light beam Lx2 based on the interbeam angle and the distance between the light projector 27 and the patient P or the table top 231. The distance is set as the AP length. Alternatively, the processing circuitry 101 may measure the interbeam distance based on the light source position of the light projector 27 corresponding to the irradiation position of the visible light beam Lx1 and the light source position of the light projector 27 corresponding to the irradiation position of the visible light beam Lx2 at a rotation angle of 90°, and may estimate the AP length based on the interbeam distance between the light projector 27 and the patient P or the table top 231. Furthermore, the processing circuitry 101 may estimate the AP length based on a predicted value of the AP length of the patient P in addition to the interbeam angle or the interbeam distance and the bed height. Upon receipt of the adjustment completion instruction, the gantry control circuitry 33 transmits the AP length to the console 100, and the memory 107 stores the AP length.

After steps SC1 through SC4, the processing circuitry 101 ends the cross-sectional shape estimation function 117-3. It is to be noted that steps SC1 and SC2 and steps SC3 and SC4 may be carried out in reverse order. In other words, the AP length may be estimated first and the LR length may be estimated later.

After step SC4, the processing circuitry 101 calculates the SSDE value based on the LR length estimated in step SC2, the AP length estimated in step SC4, and the CTDI value calculated in advance (step SC5). In step SC5, the processing circuitry 101 determines a conversion factor from the combination of the LR length and the AP length, and calculates the SSDE value by multiplying the determined conversion factor by the CTDI value. The conversion factor is determined for each combination of an LR length and an AP length. The conversion factor is not necessarily determined directly from the combination of an LR length and an AP length. For example, the processing circuitry 101 may include a table (LUT) in which the combination of an LR length and an AP length is associated with a water equivalent diameter, determine the water equivalent diameter from the combination of the LR length and the AP length utilizing the LUT, and determine the conversion factor utilizing the water equivalent diameter/conversion factor table.

After step SC5, the processing circuitry 101 directs the display 103 to display the SSDE value calculated in the step SC5 (step SC6). The user checks the displayed SSDE value, and if the SSDE value is determined to be unacceptable, reviews the imaging conditions or the like. If the SSDE value is determined to be acceptable, the user inputs imaging instructions via the input circuitry 31 or 105.

After step SC6, once the user inputs imaging instructions via the input circuitry 31 or 105, the processing circuitry 101 directs the gantry control circuitry 33 to start imaging (step SC7). The gantry control circuitry 33, which has been instructed to start imaging, synchronously controls the X-ray high voltage device 17, the data acquisition circuitry 19, the rotation actuator 21, the bed actuator 25, etc. in accordance with imaging conditions, to perform CT imaging for the patient P.

The operation flow of the X-ray computed tomography apparatus according to the third embodiment is completed with the above explanations.

In the above example, both the AP length and the LR length are measured. However, the present embodiment is not limited to this. For example, if the conversion factor is obtained from only one of the AP length and the LR length, measurement of the other one of the AP length and the LR length may be omitted. In the example described above, the distance between the visible light beam Lx1 and the visible light beam Lx2 at an angle of 0° or 180° is defined as the LR length; however, the embodiment is not limited to this. For example, the distance between the visible light beam Lx1 and the visible light beam Lx2 at another angle may be defined as the LR length in accordance with the position of the patient P on the table top 231. Similarly, in the example described above, the distance between the visible light beam Lx1 and the visible light beam Lx2 at an angle of 90° or 270° is defined as the AP length; however, the embodiment is not limited to this. For example, the distance between the visible light beam Lx1 and the visible light beam Lx2 at another angle may be defined as the AP length in accordance with the position of the patient P on the table top 231.

With the configuration described above, according to the third embodiment, the cross-sectional shape index value can be estimated on the basis of the projection light parameters of the light projector 27 at a plurality of rotation angles. In other words, when estimating the cross-sectional shape index value, the X-ray computed tomography apparatus according to the third embodiment does not require imaging for positioning. Therefore, the X-ray computed tomography apparatus according to the third embodiment can estimate the cross-sectional shape index value with less exposure to radiation of the patient P as compared to the case in which imaging for positioning is performed. Since the third embodiment does not use an optical camera, it can estimate the cross-sectional shape index value via a simpler apparatus design as compared to the first embodiment. Furthermore, unlike the first and second embodiments, the third embodiment directly estimates (measures) the AP length and the LR length by the adjustment of the radiation positions of the visible light beams by the user. Therefore, the estimation accuracy of the cross-sectional shape index value, such as the AP length and the LR length, is improved.

Fourth Embodiment

According to the first, second, and third embodiments, the X-ray computed tomography apparatus estimates the cross-sectional shape index value and calculates the SSDE value using the visible light beams projected from the light projector. However, the present embodiment is not limited to this. The fourth embodiment estimates the cross-sectional shape index value and calculates the SSDE value using infrared. Details of the fourth embodiment will be described below. In the description below, structural elements with substantially the same functions as those of the first, second, and third embodiments will be denoted by the same reference symbols, and a repetitive description will be given only where necessary.

FIG. 16 is a diagram showing a configuration of the X-ray computed tomography apparatus according to the fourth embodiment. As shown in FIG. 16, a gantry 10 according to the fourth embodiment includes an infrared emitter 35 and an optical receptor 37. The infrared emitter 35 irradiates a patient P lying on the table top with infrared. The infrared of the embodiment includes near infrared, infrared in a narrow sense, and far infrared. The infrared emitter 35 is realized, for example, by an LED (Light-Emitting Diode). The optical receptor 37 receives the infrared projected on and reflected from the patient P, and outputs an electric signal corresponding to the received infrared. The optical receptor 37 is realized, for example, by an infrared camera, in which optical sensors such as CMOS (Complementary Metal-Oxide Semiconductor) are two-dimensionally arrayed.

The gantry control circuitry 33 of the fourth embodiment realizes an infrared information measurement function 293. By the infrared information measurement function 293, the gantry control circuitry 33 measures information on the infrared received by the optical receptor 37. The information on the infrared is, for example, time of flight. The time of flight is defined by an elapsed time, from a time when the infrared emitter 35 emits infrared to a time when the optical receptor 37 receives the infrared reflected from the patient P.

Other information on the infrared that is utilized in this embodiment may include, for example, an intensity of the received infrared.

Processing circuitry 101 of the fourth embodiment executes a cross-sectional shape estimation function 117-4. By the cross-sectional shape estimation function 117-4, the processing circuitry 101 estimates a cross-sectional shape index value relating to a cross section of the patient P in an imaging range based on the information on the infrared.

Figure 17:
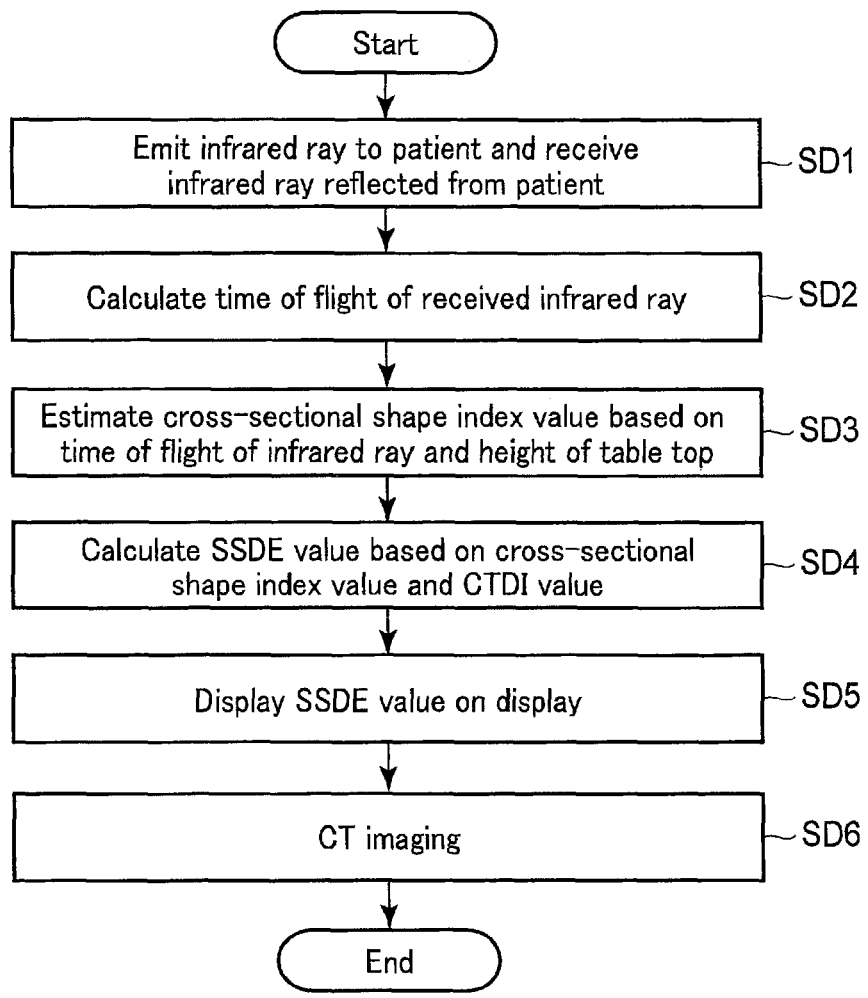
FIG. 17 is a flowchart illustrating a typical operation of the X-ray computed tomography apparatus, performed by execution of a system control function of processing circuitry according to the fourth embodiment.

FIG. 17 is a flowchart illustrating a typical operation of the X-ray computed tomography apparatus, performed by execution of a system control function 125 of the processing circuitry 101 according to the fourth embodiment. FIG. 18 is a schematic diagram illustrating an overview of estimation of a cross-sectional shape index value utilizing infrared.

As shown in FIG. 17 and FIG. 18, the processing circuitry 101 first directs the gantry control circuitry 33 to image the patient P with infrared IR. When imaging the patient P with the infrared IR, the infrared emitter 35 irradiates the patient P lying on a table top 231, and the optical receptor 37 receives the infrared reflected from the patient (step SD1). As shown in FIG. 18, the infrared emitter 35 and the optical receptor 37 are provided on a ceiling 200 of an examination room. The set of the infrared emitter 35 and the optical receptor 37 is preferably housed in a discretionary housing 39. The patient P is placed on the table top 231. Imaging of the patient P using the infrared emitter 35 and the optical receptor 37 is typically performed before the table top 231 is inserted into a bore 41 to prevent the infrared IR from being interrupted by a gantry housing 40. The infrared IR is preferably projected on the entire width of the patient P including the imaging range to measure a body thickness (AP length) and a width (LR length) of the patient P with the infrared IR.

After step SD1, the gantry control circuitry 33 executes the infrared information measurement function 293 and measures the time of flight of the infrared received by the optical receptor 37 (step SD2). In step SD2, the gantry control circuitry 33 calculates as a time of flight an elapsed time, from a time when the infrared emitter 35 emits infrared to a time when the optical receptor 37 receives the infrared reflected from the patient P.

After step SD2, the processing circuitry 101 executes the cross-sectional shape estimation function 117-4 and estimates the cross-sectional shape index value based on the time of flight of the infrared and the height of the table top 231 (Step SD3). In step SD3, the processing circuitry 101 estimates the AP length (thickness) and the LR length (width) of the patient P as the cross-sectional shape index values.

The AP length is estimated, for example, as follows. As shown in FIG. 18, the AP length of the patient P can be estimated from the propagation velocity of the infrared IR, the time of flight of the infrared IR reflected from the patient P, and time of flight of the infrared IR reflected from the table top 231 in the absence of the patient P. The time of flight of the infrared IR reflected from the table top 231 is measured or predicted in advance. For example, the gantry control circuitry 33 sets the table top 231 at a plurality of heights, directs the infrared emitter 35 to project the infrared IR on the surface of the table top at each height, and directs the optical receptor 37 to receive the infrared reflected from the surface of the table top 231. The gantry control circuitry 33 calculates a difference between the projection time when the infrared is projected and the reception time when the infrared is received, and sets the difference as the time of flight for each of the heights of the table top. The gantry control circuitry 33 produces a table in which each height of the table top is associated with the time of flight (hereinafter referred to as the time-of-flight table), and stores the table in its own memory. If the time of flight in the presence of the patient P is measured, the time of flight associated with the corresponding height of the table top is read from the time-of-flight table based on the height of the table top used in the infrared imaging. The difference between the read time of flight and the time of flight in the pretense of the patient P is calculated, and the AP length is calculated from the difference and the propagation velocity of the infrared.

The LR length is estimated, for example, as follows. The gantry control circuitry 33 causes the infrared IR to be projected and received at intervals of a specific angle to pass through the patient P lying on the table top 231, and records the reception time or the time of flight for each infrared radiation. The reception time or the time of flight changes abruptly at a boundary between the place where the patient is present and the place where the patient is not present. A position where the reception time or the time of flight abruptly changes on the right of the patient P and such a position on the left of the patient P are specified, and the distance between the specified positions on the right and left of the patient P is calculated as the LR length. The LR length may be estimated by using the optical camera 29 as used in the first and second embodiment, or by using the light projector 27 as used in the third embodiment.

After step SD3, the processing circuitry 101 calculates an SSDE value based on the LR length and the AP length estimated in step SD3 and the CTDI value measured in advance (step SD4). Step SD4 is similar to, for example, step SC5 of the third embodiment.

After step SD4, the processing circuitry 101 directs the display 103 to display the SSDE value calculated in the step SD4 (step SD5). Step SD5 is similar to, for example, step SC6 of the third embodiment.

After step SD5, once the user inputs imaging instructions via the input circuitry 31 or 105, the processing circuitry 101 directs the gantry control circuitry 33 to start imaging (step SD6). The gantry control circuitry 33, which has been instructed to start imaging, synchronously controls the X-ray high voltage device 17, the data acquisition circuitry 19, the rotation actuator 21, the bed actuator 25, etc. in accordance with imaging conditions, to perform CT imaging for the patient P.

The operation flow of the X-ray computed tomography apparatus according to the fourth embodiment is completed with the above explanations.

The fourth embodiment can be modified in various ways. For example, in the above explanations, whether or not the table top 231 is moved in CT imaging is not particularly specified. In the case of helical scan for performing a scan while moving the table top 231, and in the case of intermediate movement scan for intermittently performing a scan and moving the table top 231, the CT imaging range expands over a wide range. However, since the infrared imaging range that can be covered by one infrared imaging varies depending on the specification of the infrared emitter 35 and the optical receptor 37, the CT imaging range may not be covered by one infrared imaging. In this case, the imaging range in a wide range can be imaged by the infrared by moving the table top 231 in its long-axis direction. For example, the CT imaging range is divided into a plurality of small ranges in accordance with the imaging range of the infrared, and infrared imaging and estimation of the cross-sectional shape index value are performed in each small range. As a result, even when the CT imaging range is wide, the cross-sectional shape index value can be estimated.

Furthermore, according to the above explanation, for example, the set of the infrared emitter 35 and the optical receptor 37 is provided on the ceiling 200 of the examination room. However, the set may be provided on any other place, such as the gantry housing 40, so long as the infrared imaging of the patient P is possible. Furthermore, it is assumed that the set of the infrared emitter 35 and the optical receptor 37 is fixed to the ceiling 200. However, the set may be provided so as to be slidable along the Z axis or the X axis in the examination room, or slidable on a two-dimensional plane defined by the Z axis and the X axis. With this configuration, the infrared IR can be projected on the patient P or the table top 231 substantially at right angles. Alternatively, a plurality of sets of the infrared emitter 35 and the optical receptor 37 may be provided so as to be slidable along the Z axis or the X axis, or slidable on a two-dimensional plane defined by the Z axis and the X axis. Also with this configuration, the infrared IR can be projected on the patient P or the table top 231 substantially at right angles.

With the configuration described above, according to the fourth embodiment, the cross-sectional shape index value can be estimated by utilizing the infrared. In other words, when estimating the cross-sectional shape index value, the X-ray computed tomography apparatus according to the fourth embodiment does not require imaging for positioning. Therefore, the X-ray computed tomography apparatus according to the fourth embodiment can estimate the cross-sectional shape index value with less exposure to radiation of the patient P as compared to the case in which imaging for positioning is performed.

As described above, the X-ray computed tomography apparatus according to the embodiments includes the gantry 10, the bed 23, the light projector 27, and the processing circuitry 101. The gantry 10 performs x-ray CT imaging. The bed 23 movably supports the table top 231 on which the patient P lies. The optical emitter 27 or 35 irradiates the patient P lying on the table top 231 with light beams. The processing circuitry 101 estimates the cross-sectional shape index value of the patient P in the imaging range by utilizing light beams projected on the patient P.

With the configuration described above, the X-ray computed tomography apparatus of the embodiments estimate the cross-sectional shape index value by using the optical emitter 27 or 35 without performing imaging for positioning. Therefore, the exposure to radiation of the patient P for estimation of a cross-sectional shape can be reduced.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray computed tomography apparatus comprising:
   a gantry that performs X-ray CT imaging;
   a bed that movably supports a table top on which a subject lies;
   an optical emitter that emits a light beam to the subject lying on the table top; and
   processing circuitry that estimates a shape index value of a cross section of the subject in an imaging range by utilizing the light beam emitted to the subject; wherein
   the processing circuitry calculates an SSDE (Size-Specific Dose Estimate) value based on the shape index value and a CTDI (Computed Tomography Dose Index) value measured in advance; and
   the processing circuitry determines a correction parameter of the SSDE value based on a difference between the SSDE value and an actually measured dose value.

2. The X-ray computed tomography apparatus according to claim 1, wherein:
   the optical emitter is a light projector that projects the light beam indicating a reference line of the imaging range of CT imaging on the subject placed on the table top; and
   the processing circuitry estimates the shape index value based on a position of the light beam projected on the subject.

3. The X-ray computed tomography apparatus according to claim 2, wherein the processing circuitry estimates the shape index value of the cross section of the subject corresponding to the position of the light beam projected on the subject by applying the position of the light beam to a human body model resembling a three-dimensional shape of a human body.

4. The X-ray computed tomography apparatus according to claim 3, further comprising an optical camera that generates an optical image of the subject emitted by the light beam,
   wherein the processing circuitry specifies a first anatomical location in a light beam imaging region specified by the light beam, in a subject region relating to the subject included in the optical image, specifies a second anatomical location in the human body model corresponding to the first anatomical location, and estimates a shape index value of a cross section of the human body model at the second anatomical location as the shape index value of the cross section of the subject.

5. The X-ray computed tomography apparatus according to claim 2, wherein the light projector projects the light beam indicating an outer frame of the imaging range as the light beam indicating the reference line.

6. The X-ray computed tomography apparatus according to claim 1, wherein the processing circuitry estimates the shape index value of the cross section of the subject based on a setting parameter of the light projector that defines a radiation position of the light beam.

7. The X-ray computed tomography apparatus according to claim 6, wherein:
   the gantry supports a rotation frame that is provided with an X-ray tube and an X-ray detector and is rotatable around a rotation axis;
   the light projector is mounted on the rotation frame; and
   the processing circuitry estimates the shape index value based on a first setting parameter set when the light projector is located at a first angle around the rotation axis, and a second setting parameter set when the light projector is located at a second angle around the rotation axis.

8. The X-ray computed tomography apparatus according to claim 7, wherein:
   the light projector is configured to project a first light beam indicating a first frame line forming an outer frame of the imaging range, and a second light beam indicating a second frame line that faces the first frame line; and the processing circuitry sets the first setting parameter that defines a radiation position of the first light beam and the second setting parameter that defines a radiation position of the second light beam in accordance with user's instructions.

9. The X-ray computed tomography apparatus according to claim 1, wherein the processing circuitry corrects a shape of the cross section of the subject or the shape index value of the subject based on a correction parameter in accordance with a height of the table top.

10. The X-ray computed tomography apparatus according to claim 1, wherein the processing circuitry calculates the SSDE value based on the shape index value, the CTDI value, and the correction parameter.

11. The X-ray computed tomography apparatus according to claim 1, wherein the processing circuitry determines a modulation parameter of a tube current based on the shape index value.

12. The X-ray computed tomography apparatus according to claim 1, wherein:
the optical emitter emits infrared ray as the light beam to the subject lying on the table top; and
the processing circuitry estimates the shape index value of the cross section of the subject in the imaging range based on information on the infrared ray reflected from the subject.

13. The X-ray computed tomography apparatus according to claim 12, wherein
the processing circuitry estimates the shape index value of the cross section of the subject in the imaging range based on information on the infrared reflected from the subject and a height of the table top.

* * * * *